United States Patent [19]
Zarling et al.

[11] Patent Number: 5,763,240
[45] Date of Patent: Jun. 9, 1998

[54] IN VIVO HOMOLOGOUS SEQUENCE TARGETING IN EUKARYOTIC CELLS

[75] Inventors: David A. Zarling, Menlo Park; Elissa P. Sena, Palo Alto, both of Calif.

[73] Assignee: SRI International, Menlo Park, Calif.

[21] Appl. No.: 275,916

[22] Filed: Jul. 14, 1994

Related U.S. Application Data

[63] Continuation of Ser. No. 873,438, Apr. 24, 1992, abandoned.

[51] Int. Cl.$^6$ .................... C12N 15/64; C12N 15/90; C12Q 1/68; C12P 19/34
[52] U.S. Cl. .................... 435/172.3; 435/6; 435/91.1; 435/91.4
[58] Field of Search .................... 435/6, 91.1, 91.4, 435/172.3

[56] References Cited

U.S. PATENT DOCUMENTS 4,950,599  8/1990  Bertling .................... 435/172.3

FOREIGN PATENT DOCUMENTS

WO 93/03736  3/1993  WIPO.
WO 94/04032  3/1994  WIPO.

OTHER PUBLICATIONS

Hunger–Bertling et al. (1990), Short DNA Fragments Induce Site Specific Recombination in Mammalian Cells, Mol. Cell. Bio. 92:107–116.

Bertling (1987), Transfection of a DNA/Protein Complex into Nuclei of Mammalian Cells Using Polyoma Capsids and Electroporation, Bioscience Reports 7:107–111.

Cox and Lehman (1987), Enzymes of General Recombination, Ann. Rev. Biochem. 56:229–262.

Felgner et al. (1987), Lipofection: A highly efficient, lipid–mediated DNA–transfection Procedure, Proc. Natl. Acad. Sci. USA 84:7413–7417.

Fields and Jang (1990), Presence of a Potent Transcription Activating Sequence in the p53 Protein, Science 249:1046–1049.

Sauer and Henderson (1990), Targeted Insertion of Exogenous DNA into the Eukaryotic Genome by the Cre Recombinase, The New Biologist 2:441–449.

Valancius and Smithies (1991), Testing an "In–Out" Targeting Procedure for Making Subtle Genomic Modifications in Mouse Embryonic Stem Cells, Molecular and Cellular Biology 11:1402–1408.

Wu et al. (1989), Targeting Genes: Delivery and Persistent Expression of a Foreign Gene Driven by Mammalian Regulatory Elements in vivo, J. Biol. Chem. 264:16985–16987.

Ausubel et al., Short Protocols in Molecular Biology, 2nd ed., (John Wiley & Sons, New York, 1992), pp. 9–14 and 9–15.

Dunderdale et al. (1991), Nature 354:506–510.

Cheng et al. (1989), NATO ASI Ser., Ser. C, 272 (Photochemical Probes in Biochemistry), pp. 169–177.

*Primary Examiner*—Nancy Degen
*Attorney, Agent, or Firm*—Flehr Hohbach Test Albritton & Herbert LLP; Richard F. Trecartin; Robin M. Silva

[57] ABSTRACT

The invention relates to methods for targeting an exogenous polynucleotide or exogenous complementary polynucleotide pair to a predetermined endogenous DNA target sequence in a eukaryotic cell by homologous pairing, particularly for altering an endogenous DNA sequence, such as a chromosomal DNA sequence, typically by targeted homologous recombination. In certain embodiments, the invention relates to methods for targeting an exogenous polynucleotide having a linked chemical substituent to a predetermined endogenous DNA sequence in a metabolically active eukaryotic cell, generating a DNA sequence-specific targeting of one or more chemical substituents in an intact nucleus of a metabolically active eukaryotic cell, generally for purposes of altering a predetermined endogenous DNA sequence in the cell. The invention also relates to compositions that contain exogenous targeting polynucleotides, complementary pairs of exogenous targeting polynucleotides, chemical substituents of such polynucleotides, and recombinase proteins used in the methods of the invention.

47 Claims, 8 Drawing Sheets

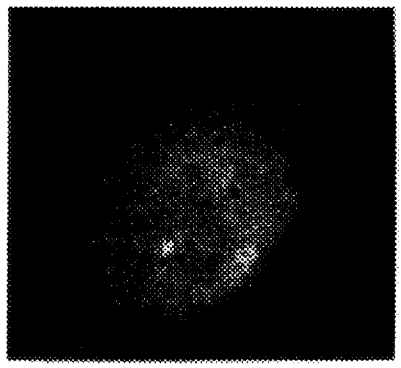
FIG._1A
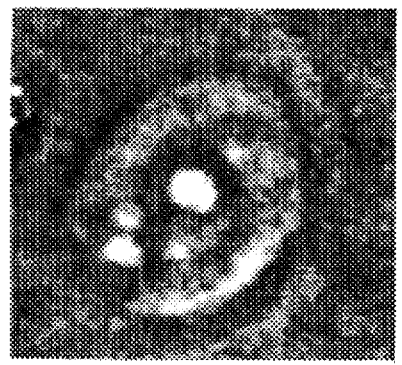
FIG._1B
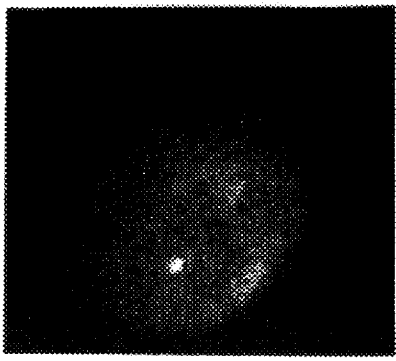
FIG._1C
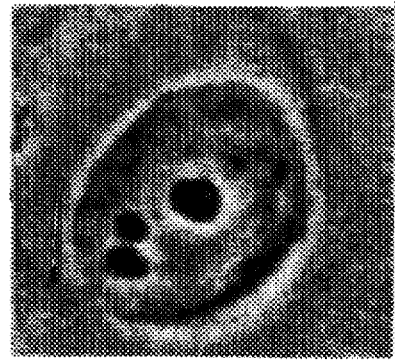
FIG._1D

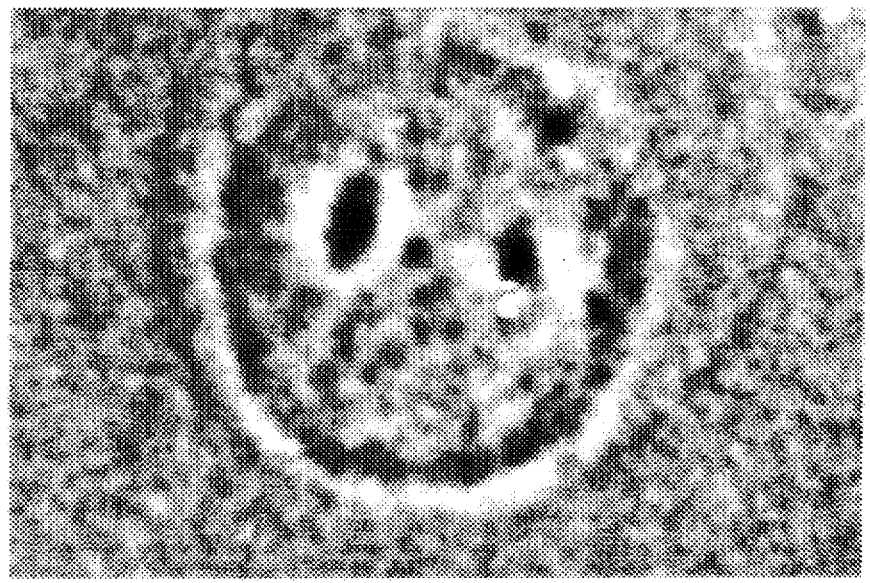
FIG._2A
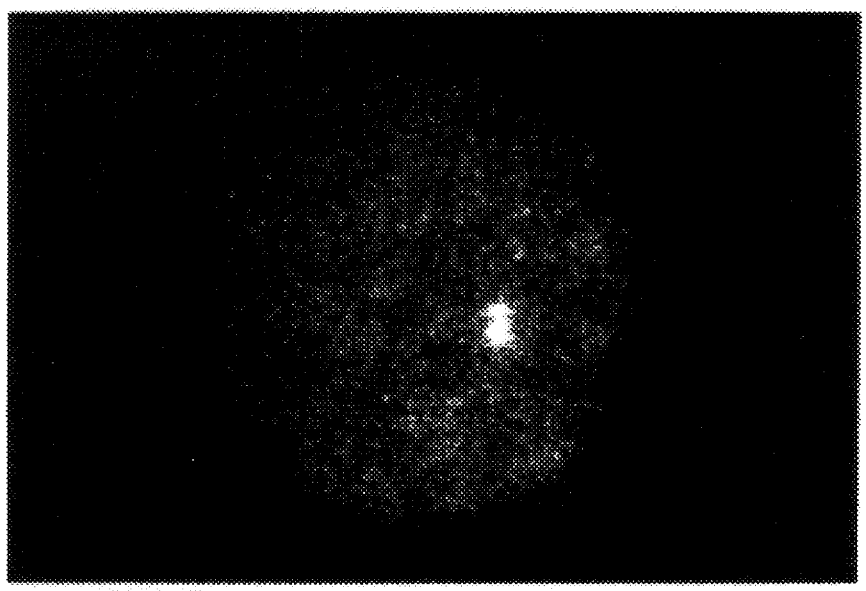
FIG._2B
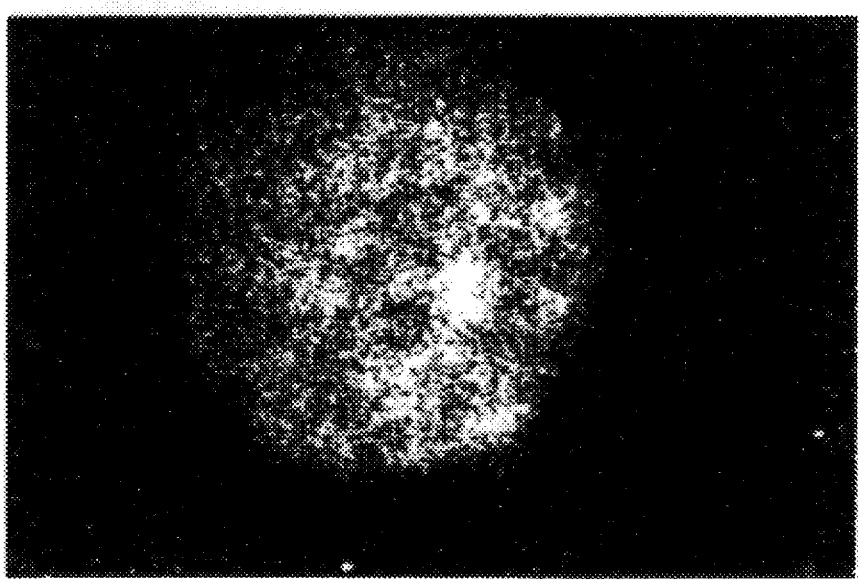
FIG._2C

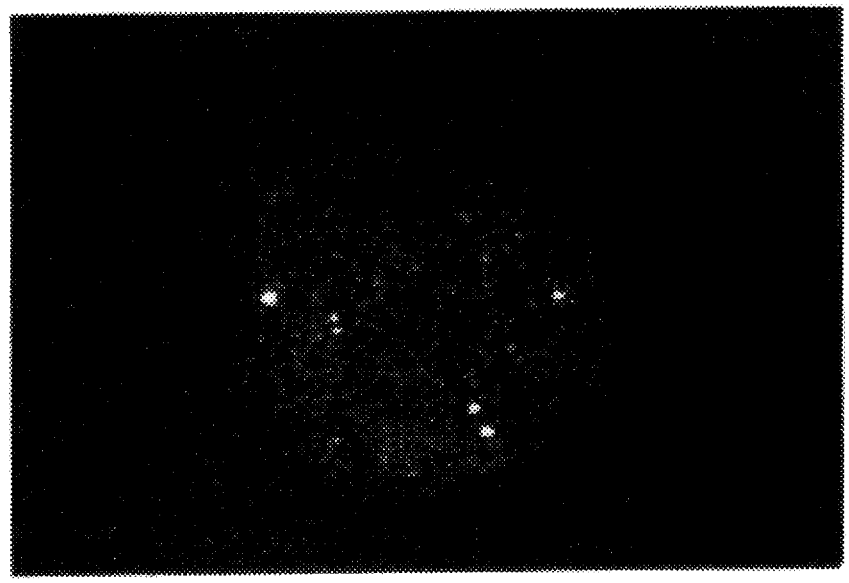
FIG._3A
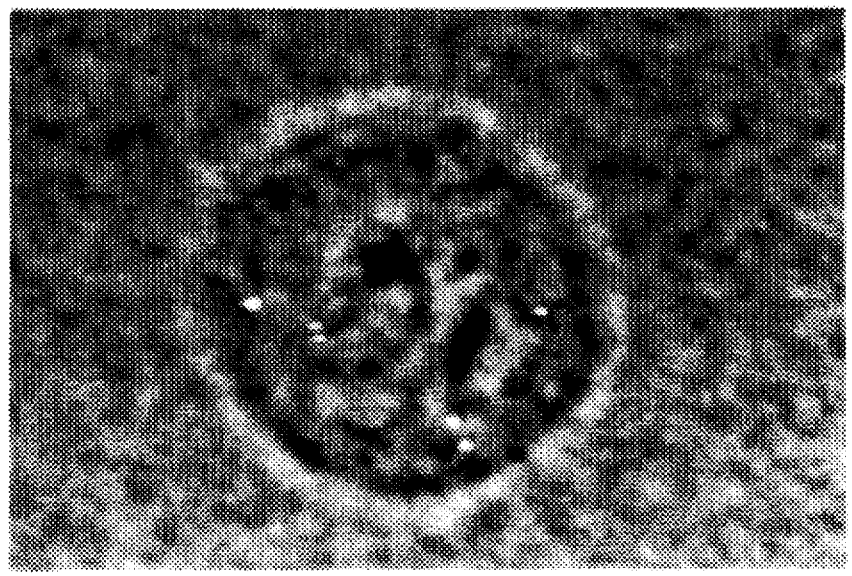
FIG._3B

FIG._4
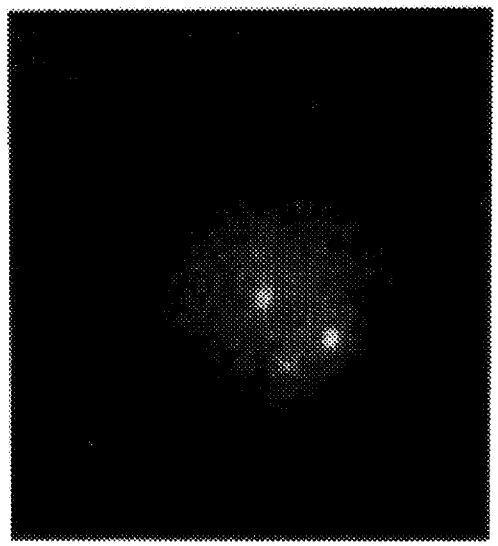
FIG._5A
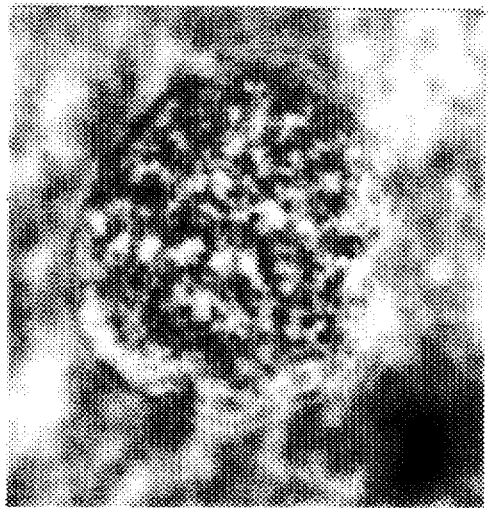
FIG._5B

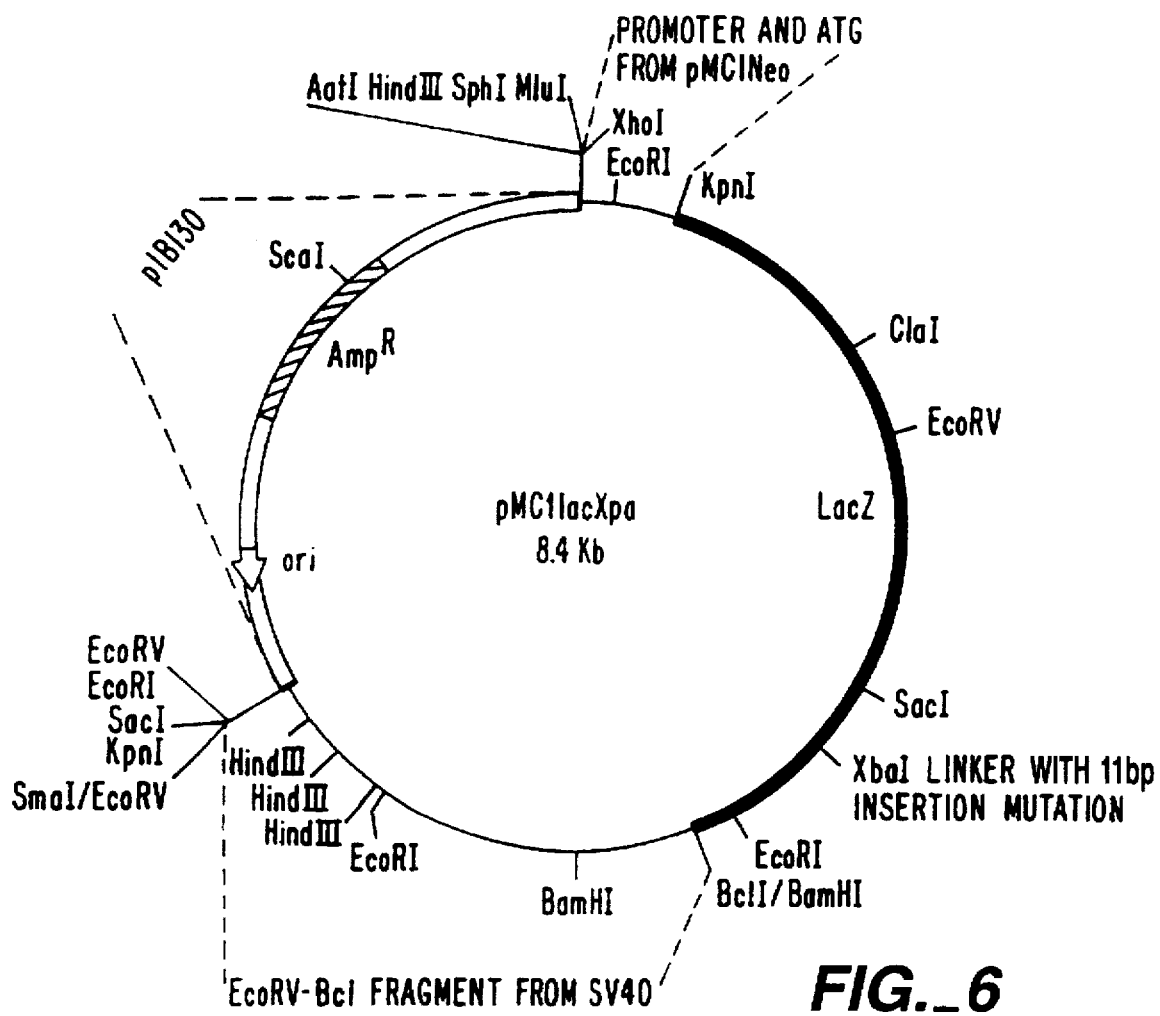
FIG._6

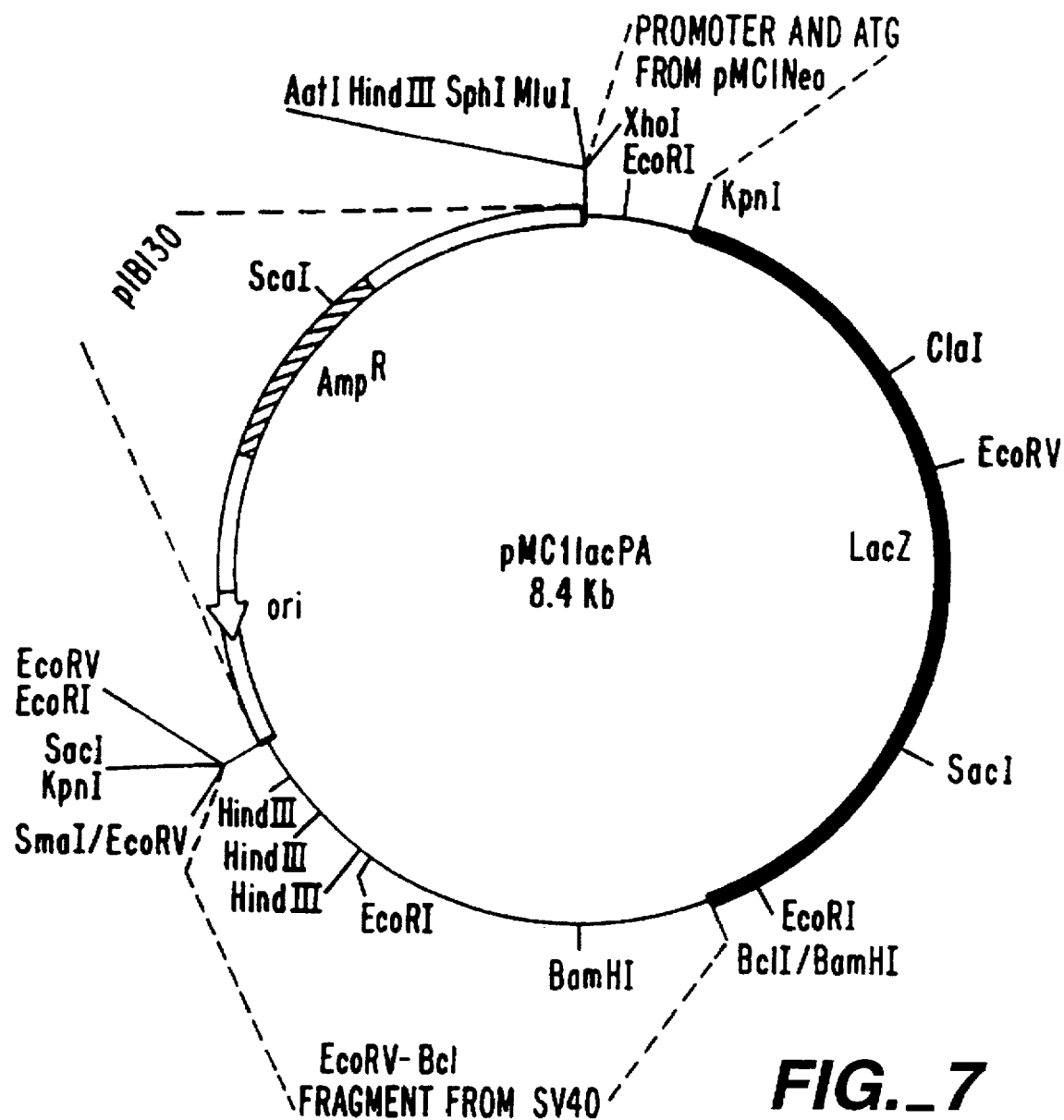
FIG._7

```
                                                        Eco RV      T7 RNA                                              Eco RI
                                                          V       POLYMERASE PROMOTER        pppGGGAGA...(RNA)-->          V
5'- ATG ATT ACG GAT ATC GAA TTA ATA CGA CTC ACT ATA GGG AGA TCG AAT TCG Sma I                       Hinc II
                   Xma I                         Acc I                       Xho I
     Sac I   Kpn I Bam HI Xba I                 Sal I            Pst I      Xpa I      Mlu I
      V       V V   V     V                     VVV                V          VV        V
    AGC TCG GTA CCC GGG GAT CCT CTA GAG CTC GAC TCG ACC TGC AGG GGC CCT CGA GAC Hind III                           T3 RNA                                 Aat I
           Sph I                            POLYMERASE PROMOTER                          V
            V V
    GCG TGG CAT GCA AGC TTT CTC CCT TTA GTG AGG GTT AAT TAT AGG CCT AGC TTG -3'
                                        <-(RNA)...AGAGGGppp
```

FIG._8

```
                              bgl I                              Hin fI
         3610      3620      3630      3640      3650      3660
      ATAAAAAACAACTGCTGACGCCGCTGCGCGATCAGTTCACCCGTGCACCGCTGGATAACG
                   ^    ^    ^  ^^    ^              ^
                   Aha IIFnu4 HIDpnI            Apa LI
                   Hga I    Cfo I
                   HgiD I   Hha I
                       Fnu4 HIAcc II
                            HinP I
                              MboI
                              Sau3A I
         3670      3680      3690      3700      3710      3720
      ACATTGGCGTAAGTGAAGCGACCCGCATTGACCCTAACGCCTGGGTCGAACGCTGGAAGG
                                                  ^    ^         ^
                                              Apy I Taq I   Fnu4 HI
                                              BstNI
                                              Eco RII
                                              ScrF I
         3730      3740      3750      3760      3770      3780
      CGGCGGGCCATTACCAGGCCGAAGCAGCGTTGTTGCAGTGCACGGCAGATACACTTGCTG
      ^^^         ^    ^    ^              ^
      DraII     Apy I    BbvI        Apa LI
      Asu I     BstNI    Fnu4 HI
      Cfr 131   Eco RII
      Sau96 I   ScrF I
         Hae III   Hae III
         Pal I     Pal I
         3790      3800      3810      3820      3830      3840
      ATGCGGTGCTGATTACGACCGCTCACGCGTGGCAGCATCAGGGGAAAACCTTATTTATCA
              ^                  ^^       ^    ^
              Hin fI          Mlu I   BbvI
                              Acc IIFnu4 HI
                                     SfaN I
         3850      3860      3870      3880      3890      3900
      GCCGGAAAACCTACCGGATTGATGGTAGTGGTCAAATGGCGATTACCGTTGATGTTGAAG
      ^         ^    ^ ^                              ^
      Hpa II    Hpa II                            Hin fI
      Msp I     Msp I
                Hin fI
         3910      3920      3930      3940      3950      3960
      TGGCGAGCGATACACCGCATCCGGCGCGGATTGGCCTGAACTGCCAGCTGGCGCAGGTAG
              ^     ^ ^^     ^    ^              ^^      ^
              SfaN I Cfo IHin fI            Pvu IICfo I
                    Hpa II    Hae III         Alu IHha I
                    Msp I     Pal I                HinP I
                    Hha I
                    HinP I
                    Acc II
         3970      3980      3990      4000      4010      4020
      CAGAGCGGGTAAACTGGCTCGGATTAGGGCCGCAAGAAAACTATCCCGACCGCCTTACTG
                   ^   ^^^                                        ^
                   Hin fIHae III                              Fnu4 HI
                        Asu I
                        Cfr 131
                        Sau96 I
                        Pal I
      _____ _____/
                                       Y
                                    FIG._9
```

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
ATGATTACGG ATATCGAATT AATACGACTC ACTATAGGGA GATCGAATTC GAGCTCGGTA      60
CCCGGGGATC CTCTAGAGTC GACCTGCACC TGCAGGGGCC CTCGAGACGC GTGGCATGCA     120
AGCTTTCTCC CTTTAGTGAG GGTTAATTAT AGGCCTAGCT TG                        162
```

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:2:

```
CGTAAGTGAA GCGACCCGCA                                                  20
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:3:

```
AGGCCAATCC GCGCCGGATG C                                                21
```

( 2 ) INFORMATION FOR SEQ ID NO:4:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
CGTAAGTGAA GCGACCCGCA TTGACCCTAA CGCCTGGGTC GAACGCTGGA AGGCGGCGGG         60

CCATTACCAG GCCGAAGCAC GGTTGTTGCA GTGCACGGCA GATACACTTG CTGATGCGGT        120

GCTGATTACG ACCGCTCACG CGTGGCAGCA TCAGGGGAAA ACCTTATTTA TCAGCCGGAA        180

AACCTACCGG ATTGATGGTA GTGGTCAAAT GGCGATTACC GTTGATGTTG AAGTGGCGAG        240

CGATACACCG CATCCGGCGC GGATTGGCCT                                        270
```

( 2 ) INFORMATION FOR SEQ ID NO:5:

( i ) SEQUENCE CHARACTERISTICS:
     ( A ) LENGTH: 281 base pairs
     ( B ) TYPE: nucleic acid
     ( C ) STRANDEDNESS: single
     ( D ) TOPOLOGY: linear ( i i ) MOLECULE TYPE: DNA (genomic)

( x i ) SEQUENCE DESCRIPTION: SEQ ID NO:5:

```
CGTAAGTGAA GCGACCCGCA TTGACCCTAA CGCCTGGGTC GAACGCTGGA AGGCGGCGGG         60

CCATTACCAG GCCGAAGCAC GGTTGTTGCA GTGCACGGCA GATACACTTG CTGATGCGGT        120

GCTGATTACG ACCGCTCACG CGCTCTAGAC GCGTGGCAGC ATCAGGGGAA AACCTTATTT        180

ATCAGCCGGA AAACCTACCG GATTGATGGT AGTGGTCAAA TGGCGATTAC CGTTGATGTT       240

GAAGTGGCGA GCGATACACC GCATCCGGCG CGGATTGGCC T                           281
```

1

IN VIVO HOMOLOGOUS SEQUENCE TARGETING IN EUKARYOTIC CELLS

This is a continuation of application Ser. No. 07/873,438 filed 24 Apr. 1992 now abandoned.

FIELD OF THE INVENTION

The invention relates to methods for targeting an exogenous polynucleotide or exogenous complementary polynucleotide pair to a predetermined endogenous DNA target sequence in a eukaryotic cell by homologous pairing, particularly for altering an endogenous DNA sequence, such as a chromosomal DNA sequence, typically by targeted homologous recombination. In certain embodiments, the invention relates to methods for targeting an exogenous polynucleotide having a linked chemical substituent to a predetermined endogenous DNA sequence in a metabolically active eukaryotic cell, generating a DNA sequence-specific targeting of one or more chemical substituents in an intact nucleus of a metabolically active eukaryotic cell, generally for purposes of altering a predetermined endogenous DNA sequence in the cell. The invention also relates to compositions that contain exogenous targeting polynucleotides, complementary pairs of exogenous targeting polynucleotides, chemical substituents of such polynucleotides, and recombinase proteins used in the methods of the invention.

BACKGROUND

Homologous recombination (or general recombination) is defined as the exchange of homologous segments anywhere along a length of two DNA molecules. An essential feature of general recombination is that the enzymes responsible for the recombination event can presumably use any pair of homologous sequences as substrates, although some types of sequence may be favored over others. Both genetic and cytological studies have indicated that such a crossing-over process occurs between pairs of homologous chromosomes during meiosis in higher organisms.

Alternatively, in site-specific recombination, exchange occurs at a specific site, as in the integration of phage λ into the *E. coli* chromosome and the excision of λ DNA from it. Site-specific recombination involves specific sequences of the phage DNA and bacterial DNA. Within these sequences there is only a short stretch of homology necessary for the recombination event, but not sufficient for it. The enzymes involved in this event generally cannot recombine other pairs of homologous (or nonhomologous) sequences, but act specifically on the particular phage and bacterial sequences.

Although both site-specific recombination and homologous recombination are useful mechanisms for genetic engineering of DNA sequences, targeted homologous recombination provides a basis for targeting and altering essentially any desired sequence in a duplex DNA molecule, such as targeting a DNA sequence in a chromosome for replacement by another sequence. Site-specific recombination has been proposed as one method to integrate transfected DNA at chromosomal locations having specific recognition sites (O'Gorman et al. (1991) *Science* 251: 1351; Onouchi et al. (1991) *Nucleic Acids Res.* 19: 6373). Unfortunately, since this approach requires the presence of specific target sequences and recombinases, its utility for targeting recombination events at any particular chromosomal location is severely limited in comparison to targeted general recombination.

For these reasons and others, targeted homologous recombination has been proposed for treating human genetic diseases. Human genetic diseases include: (1) classical human genetic diseases wherein a disease allele having a mutant genetic lesion is inherited from a parent (e.g., adenosine deaminase deficiency, sickle cell anemia, thalassemias), (2) complex genetic diseases like cancer, where the pathological state generally results from one or more specific inherited or acquired mutations, and (3) acquired genetic disease, such as an integrated provirus (e.g., hepatitis B virus). However, current methods of targeted homologous recombination are inefficient and produce desired homologous recombinants only rarely, necessitating complex cell selection schemes to identify and isolate correctly targeted recombinants.

A primary step in homologous recombination is DNA strand exchange, which involves a pairing of a DNA duplex with at least one DNA strand containing a complementary sequence to form an intermediate recombination structure containing heteroduplex DNA (see, Radding, C. M. (1982) *Ann. Rev. Genet.* 16: 405; U.S. Pat. No. 4,888,274). The heteroduplex DNA may take several forms, including a triplex form wherein a single complementary strand invades the DNA duplex (Hsieh et al. (1990) *Genes and Development* 4: 1951) and, when two complementary DNA strands pair with a DNA duplex, a classical Holliday recombination joint or chi structure (Holliday, R. (1964) *Genet. Res.* 5: 282) may form, or a double-D loop ("Diagnostic Applications of Double-D Loop Formation" U.S. patent application Ser. No. 07/755,462, filed 4 Sep. 1991, which is incorporated herein by reference). Once formed, a heteroduplex structure may be resolved by strand breakage and exchange, so that all or a portion of an invading DNA strand is spliced into a recipient DNA duplex, adding or replacing a segment of the recipient DNA duplex. Alternatively, a heteroduplex structure may result in gene conversion, wherein a sequence of an invading strand is transferred to a recipient DNA duplex by repair of mismatched bases using the invading strand as a template (*Genes*, 3rd Ed. (1987) Lewin, B., John Wiley, New York, N.Y.; Lopez et al. (1987) *Nucleic Acids Res.* 15: 5643). Whether by the mechanism of breakage and rejoining or by the mechanism(s) of gene conversion, formation of heteroduplex DNA at homologously paired joints can serve to transfer genetic sequence information from one DNA molecule to another.

The ability of homologous recombination (gene conversion and classical strand breakage/rejoining) to transfer genetic sequence information between DNA molecules makes targeted homologous recombination a powerful method in genetic engineering and gene manipulation.

The ability of mammalian and human cells to incorporate exogenous genetic material into genes residing on chromosomes has demonstrated that these cells have the general enzymatic machinery for carrying out homologous recombination required between resident and introduced sequences. These targeted recombination events can be used to correct mutations at known sites, replace genes or gene segments with defective ones, or introduce foreign genes into cells. The efficiency of such gene targeting techniques is related to several parameters: the efficiency of DNA delivery into cells, the type of DNA packaging (if any) and the size and conformation of the incoming DNA, the length and position of regions homologous to the target site (all these parameters also likely affect the ability of the incoming homologous DNA sequences to survive intracellular nuclease attack), the efficiency of recombination at particular chromosomal sites and whether recombinant events are homologous or nonhomologous. Over the past 10 years or so, several methods have been developed to introduce DNA into mammalian cells: direct needle microinjection, transfection, electroporation, retroviruses and other viral packaging and delivery systems, liposomes, and most recently techniques using DNA-coated microprojectiles delivered with a gene gun (called a biolistics device), or narrow-beam lasers (laser-poration). The processes associated with some types of gene transfer have been shown to be both mutagenic and carcinogenic (Bardwell, (1989) *Mutagenesis* 4:245), and these possibilities must be considered in choosing a transfection approach.

The choice of a particular DNA transfection procedure depends upon its availability to the researcher, the technique's efficiency with the particular chosen target cell type, and the researchers concerns about the potential for generating unwanted genome mutations. For example, retroviral integration requires dividing cells, most often results in nonhomologous recombination events, and retroviral insertion within a coding sequence of nonhomologous (i.e., non-targeted) gene could cause cell mutation by inactivating the gene's coding sequence (Friedmann, (1989) *Science* 244:1275). Newer retroviral-based DNA delivery systems are being developed using defective retroviruses. However, these disabled viruses must be packaged using helper systems, are often obtained at low titer, and recombination is still not site-specific, thus recombination between endogenous cellular retrovirus sequences and disabled virus sequences could still produce wild-type retrovirus capable of causing gene mutation. Adeno- or polyoma virus based delivery systems appear very promising (Samulski et al., (1991) *EMBO J.* 10: 3941; Gareis et al., (1991) *Cell. Molec. Biol.* 37: 191; Rosenfeld et al. (1992) *Cell* 68: 143) although they still require specific cell membrane recognition and binding characteristics for target cell entry. Liposomes often show a narrow spectrum of cell specificities, and when DNA is coated externally on to them, the DNA is often sensitive to cellular nucleases. Newer polycationic lipospermines compounds exhibit broad cell ranges (Behr et al., (1989) *Proc. Natl. Acad. Sci. USA* 86:6982) and DNA is coated by these compounds. In addition, a combination of neutral and cationic lipid has been shown to be highly efficient at transfection of animal cells and showed a broad spectrum of effectiveness in a variety of cell lines (Rose et al., (1991) *BioTechniques* 10:520). Electroporation appears to be applicable to most cell types. The efficiency of this procedure for a specific gene is variable and can range from about one event per $3 \times 10^4$ transfected cells (Thomas and Capecchi, (1987) *Cell* 51:503) to between one in $10^7$ and $10^8$ cells receiving the exogenous DNA (Koller and Smithies, (1989) *Proc. Natl. Acad. Sci. (U.S.A.)* 86: 8932). Microinjection of exogenous DNA into the nucleus has been reported to result in a very high frequency of stable transfected cells. Zimmer and Gruss (Zimmer and Gruss, (1989) *Nature* 338: 150) have reported that for the mouse hox1.1 gene, 1 per 150 microinjected cells showed a stable homologous site specific alteration.

Several methods have been developed to detect and/or select for targeted site-specific recombinants between vector DNA and the target homologous chromosomal sequence (see, Capecchi, (1989) *Science* 244:1288 for review). Cells which exhibit a specific phenotype after site-specific recombination, such as occurs with alteration of the hprt gene, can be obtained by direct selection on the appropriate growth medium. Alternatively, a selective marker sequence such as neo can be incorporated into a vector under promoter control, and successful transfection can be scored by selecting G418$^r$ cells followed by PCR to determine whether neo is at the targeted site (Joyner et al., (1989) *Nature* 338:153).

A positive-negative selection (PNS) procedure using both neo and HSV-tk genes allows selection for transfectants and against non-homologous recombination events, and significantly enriched for desired disruption events at several different mouse genes (Mansour et al., (1988) *Nature* 336:348). This procedure has the advantage that the method does not require that the targeted gene be transcribed. If the targeted gene is transcribed, a promoter-less marker gene can be incorporated into the targeting construct so that the gene become activated after homologous recombination with the target site (Jasin and Berg, (1988) *Genes and Development* 2:1353; Doetschman et al. (1988) *Proc. Natl. Acad. Sci. (U.S.A.)* 85: 8583; Dorini et al., (1989) *Science* 243:1357; Itzhaki and Porter, (1991) *Nucl. Acids Res.* 19:3835). Recombinant products produced using vectors with selectable markers often continue to retain these markers as foreign genetic material at the site of transfection, although loss does occur. Valancius and Smithies (Valancius and Smithies, (1991) *Molec. Cellular Biol.* 11:1402) have recently described an "in-out" targeting procedure that allowed a subtle 4-bp insertion modification of a mouse hprt target gene. The resulting transfectant contained only the desired modified gene sequence and no selectable marker remained after the "out" recombination step. Cotransformation of cells with two different vectors, one vector contained a selectable gene and the other used for gene disruption, increases the efficiency of isolating a specific targeting reaction (Reid et al., (1991) *Molec. Cellular Biol.* 11:2769) among selected cells that are subsequently scored for stable recombinants.

Unfortunately, exogenous sequences transferred into eukaryotic cells undergo homologous recombination with homologous endogenous sequences only at very low frequencies, and are so inefficiently recombined that large numbers of cells must be transfected, selected, and screened in order to generate a desired correctly targeted homologous recombinant (Kucherlapati et al. (1984) *Proc. Natl. Acad. Sci. (U.S.A.)* 81: 3153; Smithies, O. (1985) *Nature* 317: 230; Song et al. (1987) *Proc. Natl. Acad. Sci. (U.S.A.)* 84: 6820; Doetschman et al. (1987) *Nature* 330: 576; Kim and Smithies (1988) *Nucleic Acids Res.* 16: 8887; Doetschman et al. (1988) op.cit.; Koller and Smithies (1989) op.cit.; Shesely et al. (1991) *Proc. Natl. Acad. Sci. (U.S.A.)* 88: 4294; Kim et al. (1991) *Gene* 103: 227, which are incorporated herein by reference).

Several proteins or purified extracts having the property of promoting homologous recombination (i.e., recombinase activity) have been identified in prokaryotes and eukaryotes (Cox and Lehman (1987) *Ann. Rev. Biochem.* 56:229; Radding, C.M. (1982) op.cit.; Madiraju et al. (1988) *Proc. Natl. Acad. Sci. (U.S.A.)* 85: 6592; ; McCarthy et al. (1988) *Proc. Natl. Acad. Sci. (U.S.A.)* 85: 5854; Lopez et al. (1987) op.cit., which are incorporated herein by reference). These general recombinases presumably promote one or more steps in the formation of homologously-paired intermediates, strand-exchange, gene conversion, and/or other steps in the process of homologous recombination.

The frequency of homologous recombination in prokaryotes is significantly enhanced by the presence of recombinase activities. Several purified proteins catalzye homologous pairing and/or strand exchange in vitro, including: *E. coli* recA protein, the T4 uvsX protein, and the rec1 protein from *Ustilago maydis*. Recombinases, like the recA protein of *E. coli* are proteins which promote strand pairing and exchange. The most studied recombinase to date has been the recA recombinase of *E. coli*, which is involved in homology search and strand exchange reactions (see, Cox and Lehman (1987) op.cit.). RecA is required for induction of the SOS repair response, DNA repair, and efficient genetic recombination in *E. coli*. RecA can catalyze homologous pairing of a linear duplex DNA and a homologous single strand DNA in vitro. In contrast to site-specific recombinases, proteins like recA which are involved in general recombination recognize and promote pairing of DNA structures on the basis of shared homology, as has been shown by several in vitro experiments (Hsieh and Camerini-Otero (1989) *J. Biol. Chem.* 264: 5089; Howard-Flanders et al. (1984) *Nature* 309: 215; Stasiak et al. (1984) *Cold Spring Harbor Symp. Ouant. Biol.* 49: 561; Register et al. (1987) *J. Biol. Chem.* 262: 12812). Several investigators have used recA protein in vitro to promote homologously paired triplex DNA (Cheng et al. (1988) *J. Biol. Chem.* 263: 15110; Ferrin and Camerini-Otero (1991) *Science* 354: 1494; Ramdas et al. (1989) *J. Biol. Chem.* 264: 17395; Strobel et al. (1991) *Science* 254: 1639; Hsieh et al. (1990) op.cit.; Rigas et al. (1986) *Proc. Natl. Acad. Sci. (U.S.A.)* 83: 9591; and Camerini-Otero et al. U.S. Pat. No. 7,611,268 (available from Derwent), which are incorporated herein by reference). Unfortunately, many important genetic engineering manipulations involving homologous recombination, such as using homologous recombination to alter endogenous DNA sequences in a living cell, cannot be done in vitro. Further, gene therapy requires highly efficient homologous recombination of targeting vectors with predetermined endogenous target sequences, since selectable marker selection schemes such as those currently available in the art are not usually practicable in human beings.

Thus, there exists a need in the art for methods of efficiently altering predetermined endogenous genetic sequences by homologous pairing and homologous recombination in vivo by introducing one or more exogenous targeting polynucleotide(s) that efficiently and specifically homologously pair with a predetermined endogenous DNA sequence.

SUMMARY OF THE INVENTION

It is an object of the present invention to provide methods for targeting an exogenous polynucleotide to a predetermined endogenous DNA target sequence in a eukaryotic cell with high efficiency and with sequence specificity. Exogenous polynucleotides, are localized (or targeted) to one or more predetermined DNA target sequence(s) by homologous pairing in vivo. Such targeted homologous pairing of exogenous polynucleotides to endogenous DNA sequences in vivo may be used: (1) to target chemical substituents in a sequence-specific manner in vivo, (2) to correct or to generate genetic mutations in endogenous DNA sequences by homologous recombination and/or gene conversion, (3) to produce homologously targeted transgenic animals at high efficiency, and (4) in other applications (e.g., targeted drug delivery) based on in vivo homologous pairing.

In one embodiment, at least one exogenous polynucleotide is targeted to a predetermined endogenous DNA sequence and alters the endogenous DNA sequence, such as a chromosomal DNA sequence, typically by targeted homologous recombination within and/or flanking the predetermined endogenous DNA sequence. Generally, two complementary exogenous polynucleotides are used for targeting an endogenous DNA sequence. Typically, the targeting polynucleotide(s) are introduced simultaneously or contemporaneously with one or more recombinase species. Alternatively, one or more recombinase species may be produced in vivo by expression of a heterologous expression cassette in a cell containing the preselected target DNA sequence.

It is another object of the invention to provide methods whereby at least one exogenous polynucleotide containing a chemical substituent can be targeted to a predetermined endogenous DNA sequence in a metabolically-active eukaryotic cell, permitting sequence-specific targeting of chemical substituents such as, for example: cross-linking agents, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, base-modification agents, immunoglobulin chains, oligonucleotides, and other substituents. The methods of the invention can be used to target such a chemical substituent to a predetermined DNA sequence by homologous pairing for various applications, for example: producing sequence-specific strand scission(s), producing sequence-specific chemical modifications (e.g., base methylation, strand cross-linking), producing sequence-specific localization of polypeptides (e.g., topoisomerases, helicases, proteases), producing sequence-specific localization of polynucleotides (e.g., loading sites for transcription factors and/or RNA polymerase), and other applications.

It is another object of the present invention to provide methods for correcting a genetic mutation in an endogenous DNA target sequence, such as a sequence encoding a protein. For example, the invention can be used to correct genetic mutations, such as base substitutions, additions, and/or deletions, by converting a mutant DNA sequence that encodes a non-functional, dysfunctional, and/or truncated polypeptide into a corrected DNA sequence that encodes a functional polypeptide (e.g., has a biological activity such as an enzymatic activity, hormone function, or other biological property). The methods and compositions of the invention may also be used to correct genetic mutations or dysfunctional alleles with genetic lesions in non-coding sequences (e.g., promoters, enhancers, silencers, origins of replication, splicing signals). In contradistinction, the invention also can be used to target DNA sequences for inactivating gene expression; a targeting polynucleotide can be employed to make a targeted base substitution, addition, and/or deletion in a structural or regulatory endogenous DNA sequence to alter expression of one or more genes, typically by knocking out at least one allele of a gene (i.e., making a mutant, nonfunctional allele).

It is a further object of the invention to provide compositions that contain exogenous targeting polynucleotides, complementary pairs of targeting polynucleotides, chemical substituents of such polynucleotides, and recombinase proteins used in the methods of the invention.

BRIEF DESCRIPTION OF THE DRAWINGS

FIG. 1. Homologous targeting of recA-coated chromosome 1 alpha-satellite polynucleotides in living cell nuclei. The homologously targeted biotinylated polynucleotides were visualized by addition of FITC-avidin followed by washing to remove unbound FITC. Signals were visualized using CLSM and filters for FITC detection. Top left—localized FITC signals in cell nucleus. Lower left—enhanced image of FITC signals in cell nucleus. Upper right—overlayed image of FITC signals on phase image of nucleus. Lower right—phase image of center of cell nucleus showing nucleoli. Note: all images except lower right were photographed at same focus level (focus unchanged between these photos).

FIG. 2. Homologous targeting of recA-coated chromosome 1 alpha-satellite polynucleotides in living cell nuclei.

Bottom—fluorescent image of FITC signals in cell nucleus. Middle—enhanced image of FITC signal in cell nucleus. Top—overlay of FITC signals on phase image of nucleus.

FIG. 3. Extended DNA from a targeted human chromosome 1 in a living cell nucleus displaying repeated alpha-satellite DNA sequences visualized by FITC labeling.

FIG. 4. FITC—localization of recA-coated polynucleotides targeted to human chromosome 1 alpha-satellite sequences in a living cell nucleus. Top—image of enhanced FITC-segments. Bottom—overlay of FITC-signals on phase contrast image of cell nucleus.

FIG. 5. Human p53 tumor suppressor gene targeting in HEp-2 cells.

FIG. 6. Map of mammalian expression lacZ plasmid pMC11acXpa.

FIG. 7. Map of mammalian expression lacZ plasmid pMC11acpA.

FIG. 8. Multiple cloning site of plasmid pIBI30 (SEQ. ID. NO: 1)

FIG. 9. PCR products and primers from lacZ gene sequence SEQ. ID. NOS: 2,3,4,5.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology-A Synthesis*, 2nd Edition, E. S. Golub and D. R. Green, Eds., Sinauer Associates, Sunderland, Mass. (1991), which is incorporated herein by reference).

As used herein, the terms "predetermined endogenous DNA sequence" and "predetermined target sequence" refer to polynucleotide sequences contained in a eukaryotic cell. Such sequences include, for example, chromosomal sequences (e.g., structural genes, promoters, enhancers, recombinatorial hotspots, repeat sequences, integrated proviral sequences), episomal sequences (e.g., replicable plasmids or viral replication intermediates), chloroplast and mitochondrial DNA sequences. By "predetermined" it is meant that the target sequence may be selected at the discretion of the practitioner on the basis of known or predicted sequence information, and is not constrained to specific sites recognized by certain site-specific recombinases (e.g., FLP recombinase or CRE recombinase). In some embodiments, the predetermined endogenous DNA target sequence will be other than a naturally occurring germline DNA sequence (e.g., a transgene, parasitic, or mycoplasmal or viral sequence). An exogenous polynucleotide is a polynucleotide which is transferred into a eukaryotic cell but which has not been replicated in that host cell; for example, a virus genome polynucleotide that enters a cell by fusion of a virion to the cell is an exogenous polynucleotide, however, replicated copies of the viral polynucleotide subsequently made in the infected cell are endogenous sequences (and may, for example, become integrated into a cell chromosome). Similarly, transgenes which are microinjected into a cell are exogenous polynucleotides, however integrated and replicated copies of the transgene(s) are endogenous sequences.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The terms "substantially corresponds to" or "substantial identity" as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. "Substantially complementary" as used herein refers to a sequence that is complementary to a sequence that substantially corresponds to a reference sequence. In general, targeting efficiency increases with the length of the targeting polynucleotide portion that is substantially complementary to a reference sequence present in the target DNA.

"Specific hybridization" is defined herein as the formation of hybrids between a targeting polynucleotide (e.g., a polynucleotide of the invention which may include substitutions, deletion, and/or additions as compared to the predetermined target DNA sequence) and a predetermined target DNA, wherein the targeting polynucleotide preferentially hybridizes to the predetermined target DNA such that, for example, at least one discrete band can be identified on a Southern blot of DNA prepared from eukaryotic cells that contain the target DNA sequence, and/or a targeting polynucleotide in an intact nucleus localizes to a discrete chromosomal location characteristic of a unique or repetitive sequence. In some instances, a target sequence may be present in more than one target polynucleotide species (e.g., a particular target sequence may occur in multiple members of a gene family or in a known repetitive sequence). It is evident that optimal hybridization conditions will vary depending upon the sequence composition and length(s) of the targeting polynucleotide(s) and target(s), and the experimental method selected by the practitioner. Various guidelines may be used to select appropriate hybridization conditions (see, Maniatis et al., *Molecular Cloning: A Laboratory Manual* (1989), 2nd Ed., Cold Spring Harbor, N.Y. and Berger and Kimmel, *Methods in Enzymology*, Volume 152, *Guide to Molecular Cloning Techniques* (1987), Academic Press, Inc., San Diego, Calif., which are incorporated herein by reference. Methods for hybridizing a targeting polynucleotide to a discrete chromosomal location in intact nuclei are provided herein in the Detailed Description.

The term "naturally-occurring" as used herein as applied to an object refers to the fact that an object can be found in nature. For example, a polynucleotide sequence that is present in an organism (including viruses) that can be isolated from a source in nature and which has not been intentionally modified by man in the laboratory is naturally-occurring.

A metabolically-active cell is a cell, comprising an intact nucleus, which, when provided nutrients and incubated in an appropriate medium carries out DNA synthesis and RNA for extended periods (e.g., at least 12–24 hours). Such metabolically-active cells are typically differentiated cells incapable of further cell division (although nuclear division and chromosomal replication may occur), although stem cells are also metabolically-active cells.

DETAILED DESCRIPTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgenesis. Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Transgenic mice are derived according to Hogan, et al., "Manipulating the Mouse Embryo: A Laboratory Manual", Cold Spring Harbor Laboratory (1988) which is incorporated herein by reference.

Embryonic stem cells are manipulated according to published procedures (Teratocarcinomas and embryonic stem cells: a practical approach, E. J. Robertson, ed., IRL Press, Washington, D.C., 1987; Zjilstra et al., *Nature* 342:435–438 (1989); and Schwartzberg et al., *Science* 246:799–803 (1989), each of which is incorporated herein by reference).

Oligonucleotides can be synthesized on an Applied Bio Systems oligonucleotide synthesizer according to specifications provided by the manufacturer.

Targeting Polynucleotides

Targeting polynucleotides may be produced by chemical synthesis of oligonucleotides, nick-translation of a double-stranded DNA template, polymerase chain-reaction amplification of a sequence (or ligase chain reaction amplification), purification of prokaryotic or eukaryotic cloning vectors harboring a sequence of interest (e.g., a cloned cDNA or genomic clone, or portion thereof) such as plasmids, phagemids, YACs, cosmids, bacteriophage DNA, other viral DNA or replication intermediates, or purified restriction fragments thereof, as well as other sources of single and double-stranded polynucleotides having a desired nucleotide sequence. Targeting polynucleotides are generally ssDNA or dsDNA.

Targeting polynucleotides are generally at least about 50 to 100 nucleotides long, preferably at least about 250 to 500 nucleotides long, more preferably at least about 1000 to 2000 nucleotides long, or longer; however, as the length of a targeting polynucleotide increases beyond about 20,000 to 50,000 nucleotides, the efficiency of transferring an intact targeting polynucleotide into the cell decreases. The length of homology may be selected at the discretion of the practitioner on the basis of the sequence composition and complexity of the predetermined endogenous target DNA sequence(s) and guidance provided in the art, which generally indicates that 1.3 to 6.8 kilobase segments of homology are preferred (Hasty et al. (1991) *Molec. Cell. Biol.* 11: 5586; Shulman et al. (1990) *Molec. Cell. Biol.* 10: 4466, which are incorporated herein by reference). Targeting polynucleotides have at least one sequence that substantially corresponds to, or is substantially complementary to, a predetermined endogenous DNA sequence (i.e., a DNA sequence of a polynucleotide located in a eukaryotic cell, such as a chromosomal, mitochondrial, chloroplast, viral, episomal, mycoplasmal polynucleotide). Such targeting polynucleotide sequences serve as templates for homologous pairing with the predetermined endogenous sequence (s), and are also referred to herein as homology clamps. In targeting polynucleotides, such homology clamps are typically located at or near the 5' or 3' end, preferably homology clamps are located at each end of the polynucleotide (Berinstein et al. (1992) *Molec. Cell. Biol.* 12: 360, which is incorporated herein by reference).

The formation of heteroduplex joints is not a stringent process; genetic evidence supports the view that the classical phenomena of meiotic gene conversion and aberrant meiotic segregation result in part from the inclusion of mismatched base pairs in heteroduplex joints, and the subsequent correction of some of these mismatched base pairs before replication. Observations on recA protein have provided information on parameters that affect the discrimination of relatedness from perfect or near-perfect homology and that affect the inclusion of mismatched base pairs in heteroduplex joints. The ability of recA protein to drive strand exchange past all single base-pair mismatches and to form extensively mismatched joints in superhelical DNA reflect its role in recombination and gene conversion. This error-prone process may also be related to its role in mutagenesis. RecA-mediated pairing reactions involving DNA of $\phi$X174 and G4, which are about 70 percent homologous, have yielded homologous recombinants (Cunningham et al. (1981) *Cell* 24: 213), although recA preferentially forms homologous joints between highly homologous sequences, and is implicated as mediating a homology search process between an invading DNA strand and a recipient DNA strand, producing relatively stable heteroduplexes at regions of high homology.

Therefore, it is preferred that targeting polynucleotides of the invention have homology clamps that are highly homologous to the predetermined target endogenous DNA sequence(s). Typically, targeting polynucleotides of the invention have at least one homology clamp that is at least about 25 to 35 nucleotides long, and it is preferable that homology clamps are at least about 50 to 100 nucleotides long, and more preferably at least about 100–500 nucleotides long, although the degree of sequence homology between the homology clamp and the targeted sequence and the base composition of the targeted sequence will determine the optimal and minimal clamp lengths (e.g., G-C rich sequences are typically more thermodynamically stable and will generally require shorter clamp length). Therefore, both homology clamp length and the degree of sequence homology can only be determined with reference to a particular predetermined sequence, but homology clamps generally must be at least about 50 nucleotides long and must also substantially correspond or be substantially complementary to a predetermined target sequence. Preferably, a homology clamp is at least about 50 nucleotides long and is identical to or complementary to a predetermined target sequence.

The invention is preferably practiced with a complementary pair of targeting polynucleotides, usually of equal length, which are simultaneously or contemporaneously introduced into a eukaryotic cell harboring a predetermined endogenous target sequence, generally with at least one recombinase protein (e.g., recA). Under most circumstances, it is preferred that the targeting ppolynucleotides are incubated with recA or other recombinase prior to introduction into a eukaryotic cell, so that the recombinase protein(s) may be "loaded" onto the targeting polynucleotide(s). Incubation conditions for such recombinase loading are described in U.S. patent application Ser. No. 07/755,462, filed 4 Sep. 1991 and U.S. patent application Ser. No. 07/520,321, filed 7 May 1990, both of which are incorporated herein by reference. It is also preferred that a targeting polynucleotide contain a sequence that enhances the loading process of a recombinase, for example a recA loading sequence is the recombinogenic nucleation sequence poly-d(AC), and its complement, poly-d(GT). The duplex sequence poly[d(AC) *d(GT)]$_n$, where n is from 5 to 25, is a middle repetitive element in eukaryotic DNA.

The invention may also be practiced with individual targeting polynucleotides which do not comprise part of a complementary pair. In each case, a targeting polynucleotide is introduced into a eukaryotic cell simultaneously or contemporaneously with a recombinase protein, typically in the form of a coated targeting polynucleotide (i.e., a polynucleotide preincubated with recombinase wherein the recombinase is noncovalently bound to the polynucleotide).

A targeting polynucleotide used in a method of the invention typically is a single-stranded nucleic acid, usually a DNA strand, or derived by denaturation of a duplex DNA, which is complementary to one (or both) strand(s) of the target duplex nucleic acid. The homology clamp sequence preferably contains at least 90-95% sequence homology with the target sequence, to insure sequence-specific targeting of the targeting polynucleotide to the endogenous DNA target. The single-stranded targeting polynucleotide is typically about 50-600 bases long, although a shorter or longer polynucleotide may also be employed. Alternatively, the targeting polynucleotide may be prepared in single-stranded form by oligonucleotide synthesis methods, which may require for larger targeting polynucleotides, forming subfragments of the targeting polynucleotide, then piecing the subfragments together, typically by enzymatic ligation.

Recombinase Proteins

Recombinases are proteins that, when included with an exogenous targeting polynucleotide, provide a measurable increase in the recombination frequency and/or localization frequency between the targeting polynucleotide and an endogenous predetermined DNA sequence. In the present invention recombinase refers to a family of RecA-like recombination proteins all having essentially all or most of the same functions, particularly: (i) the protein's ability to properly position targeting polynucleotides on their homologous targets and (ii) the ability of recA protein/targeting polynucleotide complexes to efficiently find and bind to complementary endogenous sequences. The best characterized recA protein is from E. coli, in addition to the wild-type protein a number of mutant recA-like proteins have been identified (e.g., recA803). Further, many organisms have recA-like strand-transfer proteins (e.g., Fugisawa et al., (1985) Nucl. Acids Res. 13: 7473; Hsieh et al., (1986) Cell 44: 885; Hsieh et al., (1989) J. Biol. Chem. 264: 5089; Fishel et al., (1988) Proc. Natl. Acad. Sci. USA 85: 3683; Cassuto et al., (1987) Mol. Gen. Genet. 208: 10; Ganea et al., (1987) Mol. Cell Biol. 7: 3124; Moore et al., (1990) J. Biol. Chem. 19: 11108; Keene et al., (1984) Nucl. Acids Res. 12: 3057; Kimiec, (1984) Cold Spring Harbor Symp. 48:675; Kimeic, (1986) Cell 44: 545; Kolodner et al., (1987) Proc. Natl. Acad. Sci. USA 84 :5560; Sugino et al., (1985) Proc. Natl. Acad. Sci. USA 85: 3683; Halbrook et al., (1989) J. Biol. Chem. 264: 21403; Eisen et al., (1988) Proc. Natl. Acad. Sci. USA 85: 7481; McCarthy et al., (1988) Proc. Natl. Acad. Sci. USA 85: 5854; Lowenhaupt et al., (1989) J. Biol. Chem. 264: 20568, which are incorporated herein by reference. Examples of such recombinase proteins include, for example but not limitation: recA, recA803 and other recA mutants (Roca, A.I. (1990) Crit. Rev. Biochem. Molec. Biol. 25: 415), sep1 (Kolodner et al. (1987) Proc. Natl. Acad. Sci. (U.S.A.) 84: 5560; Tishkoff et al. Molec. Cell. Biol. 11: 2593), RuvC (Dunderdale et al. (1991) Nature 354: 506), DST2, KEM1, XRN1 (Dykstra et al. (1991) Molec. Cell. Biol. 11: 2583), STPα/DST1 (Clark et al. (1991) Molec. Cell. Biol. 11: 2576), HPP-1 (Moore et al. (1991) Proc. Natl. Acad. Sci. (U.S.A.) 88: 9067), and uvsX. RecA may be purified from E. coli strains, such as E. coli strains JC12772 and JC15369 (available from A. J. Clark and M. Madiraju, University of California-Berkeley). These strains contain the recA coding sequences on a "runaway" replicating plasmid vector present at a high copy numbers per cell. The recA803 protein is a high-activity mutant of wildtype recA. The art teaches several examples of recombinase proteins from Drosophila, plant, human, and non-human mammalian cells, including proteins with biological properties similar to recA (i.e., recA-like recombinases).

Recombinase protein(s) may be exogenously administered to a eukaryotic cell simultaneously or contemporaneously (i.e., within about a few hours) with the targeting polynucleotide(s). Such administration is typically done by microinjection, although electroporation, lipofection, and other methods known in the art may also be used. Alternatively, recombinase proteins may be produced in vivo from a heterologous expression cassette in a transfectant cell or transgenic cell, such as a transgenic totipotent embryonal stem cell (e.g., a murine ES cell such as AB-1) used to generate a transgenic non-human animal line or a pluripotent hematopoietic stem cell for reconstituting all or part of the hematopoietic stem cell population of an individual. Conveniently, a heterologous expression cassette includes a modulatable promoter, such as an ecdysone-inducible promoter-enhancer combination, an estrogen-induced promoter-enhancer combination, a CMV promoter-enhancer, an insulin gene promoter, or other cell-type specific, developmental stage-specific, hormone-inducible, or other modulatable promoter construct so that expression of at least one species of recombinase protein from the cassette can by modulated for transiently producing recombinase(s) in vivo simultaneous or contemporaneous with introduction of a targeting polynucleotide into the cell. When a hormone-inducible promoter-enhancer combination is used, the cell must have the required hormone receptor present, either naturally or as a consequence of expression a co-transfected expression vector encoding such receptor.

For making transgenic non-human animals (which include homologously targeted non-human animals) embryonal stem cells (ES cells) are preferred. Murine ES cells, such as AB-1 line grown on mitotically inactive SNL76/7 cell feeder layers (McMahon and Bradley, Cell 62:1073-1085 (1990)) essentially as described (Robertson, E. J. (1987) in Teratocarcinomas and Embryonic Stem Cells: A Practical Approach. E. J. Robertson, ed. (Oxford: IRL Press), p. 71–112) may be used for homologous gene targeting. Other suitable ES lines include, but are not limited to, the E14 line (Hooper et al. (1987) Nature 326: 292–295), the D3 line (Doetschman et al. (1985) J. Embryol. Exp. Morph. 87: 27–45), and the CCE line (Robertson et al. (1986) Nature 323: 445–448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal).

The pluripotence of any given ES cell line can vary with time in culture and the care with which it has been handled. The only definitive assay for pluripotence is to determine whether the specific population of ES cells to be used for targeting can give rise to chimeras capable of germline transmission of the ES genome. For this reason, prior to gene targeting, a portion of the parental population of AB-1 cells is injected into C57Bl/6J blastocysts to ascertain whether the cells are capable of generating chimeric mice with extensive ES cell contribution and whether the majority of these chimeras can transmit the ES genome to progeny.

The vectors containing the DNA segments of interest can be transferred into the host cell by well-known methods, depending on the type of cellular host. For example, microinjection is commonly utilized for eukaryotic cells, although calcium phosphate treatment, electroporation, lipofection, biolistics or viral-based transfection also may be used. Other methods used to transform mammalian cells include the use of Polybrene, protoplast fusion, and others (see, generally, Sambrook et al. Molecular Cloning: A Laboratory Manual, 2d ed., 1989, Cold Spring Harbor Laboratory Press, Cold Spring Harbor, N.Y., which is incorporated herein by reference). Direct injection of DNA and/or recombinase-coated targeting polynucleotides into target cells, such as skeletal or muscle cells also may be used (Wolff et al. (1990) *Science* 247: 1465, which is incorporated herein by reference).

RecA protein is typically obtained from bacterial strains that overproduce the protein: wild-type *E. coli* recA protein and mutant recA803 protein may be purified from such strains. Alternatively, recA protein can also be purchased from, for example, Pharmacia (Piscataway, N.J.).

RecA protein forms a nucleoprotein filament when it coats a single-stranded DNA. In this nucleoprotein filament, one monomer of recA protein is bound to about 3 nucleotides. This property of recA to coat single-stranded DNA is essentially sequence independent, although particular sequences favor initial loading of recA onto a polynucleotide (e.g., nucleation sequences). The nucleoprotein filament(s) can be formed on essentially any DNA molecule and can be formed in cells (e.g., mammalian cells), forming complexes with both single-stranded and double-stranded DNA.

The conditions used to coat targeting polynucleotides with recA protein and ATPγS have been described in U.S. patent application Ser. No. 07/755,462, filed 4 Sep. 1991 and U.S. patent application Ser. No. 07/520,321, filed 7 May 1990. Alternatively, targeting polynucleotides can be coated using GTPγS, mixes of ATPγS and rATP and/or DATP, or dATP or rATP alone in the presence of rATP generating system (Boehringer Mannheim). Various mixtures of GTPγS, ATPγS, ATP DATP and/or rATP may be used, particularly mixes of ATPγS and ATP.

RecA protein coating of targeting polynucleotides is typically carried out as described in U.S. patent application Ser. No. 07/755,462, filed 4 Sep. 1991, which is incorporated herein by reference. Briefly, the targeting polynucleotide, whether double-stranded or single-stranded, is denatured by heating in an aqueous solution at 95°–100° C. for five minutes, then placed in an ice bath for one minute followed by centrifugation at 0° C. for approximately 20 sec, before use. When denatured targeting polynucleotides are not placed in a freezer at −20° C. they are usually immediately added to standard recA coating reaction buffer containing ATPγS, at room temperature, and to this is added the recA protein.

RecA coating of targeting polynucleotide(s) is initiated by incubating polynucleotide-recA mixtures at 37° C. for 10 min. RecA protein concentration tested during reaction with polynucleotide varies depending upon polynucleotide size and the amount of added polynucleotide, and the ration of recA molecule:nucleotide preferably ranges between about 3:1 and 1:3. When single-stranded polynucleotides are recA coated independently of their homologous polynucleotide strands, the mM and μM concentrations of ATPγS and recA, respectively, can be reduced to one-half those used with double-stranded targeting polynucleotides (i.e. recA and ATPγS concentration ratios are usually kept constant at a specific concentration of individual polynucleotide strand, depending on whether a single- or double-stranded polynucleotide is used).

The coating of targeting polynucleotides with recA protein can be evaluated in a number of ways. First, protein binding to DNA can be examined using band-shift gel assays (McEntee et al., (1981) *J. Biol. Chem.* 256:8835). Labeled polynucleotides can be coated with recA protein in the presence of ATPγS and the products of the coating reactions may be separated by agarose gel electrophoresis. Following incubation of recA protein with denatured duplex DNAs the recA protein effectively coats single-stranded targeting polynucleotides derived from denaturing a duplex DNA. As the ratio of recA protein monomers to nucleotides in the targeting polynucleotide increases from 0, 1:27, 1:2.7 to 3.7:1 for 121-mer and 0, 1:22, 1:2.2 to 4.5:1 for 159-mer, targeting polynucleotide's electrophoretic mobility decreases, i.e., is retarded, due to recA-binding to the targeting polynucleotide. Retardation of the coated polynucleotide's mobility reflects the saturation of targeting polynucleotide with recA protein. An excess of recA monomers to DNA nucleotides is required for efficient recA coating of short targeting polynucleotides (Leahy et al., (1986) *J. Biol. Chem.* 261:6954).

A second method for evaluating protein binding to DNA is in the use of nitrocellulose fiber binding assays (Leahy et al., (1986) *J. Biol. Chem.* 261:6954; Woodbury, et al., (1983) *Biochemistry* 22(20):4730–4737. The nitrocellulose filter binding method is particularly useful in determining the dissociation-rates for protein:DNA conplexes using labeled DNA. In the filter binding assay, DNA:protein complexes are retained on a filter while free DNA passes through the filter. This assay method is more quantitative for dissociation-rate determinations because the separation of DNA:protein complexes from free targeting polynucleotide is very rapid.

Targeting of Endogenous DNA Sequences In Vivo

Generally, any predetermined endogenous DNA sequence can be altered by homologous recombination (which includes gene conversion) with an exogenous targeting polynucleotide (or complementary pair of targeting polynucleotides) that has at least one homology clamp which substantially corresponds to or is substantially complementary to a predetermined endogenous DNA target sequence and which is introduced with a recombinase (e.g., recA) into a eukaryotic cell having the predetermined endogenous DNA sequence. Typically, a targeting polynucleotide (or complementary polynucleotide pair) has a portion having a sequence that is not present in the preselected endogenous targeted sequence(s) (i.e., a nonhomologous portion) which may be as small as a single mismatched nucleotide or may span up to about several kilobases or more of nonhomologous sequence. Generally, such nonhomologous portions are flanked on each side by homology clamps, although a single flanking homology clamp may be used. Nonhomologous portions are used to make insertions, deletions, and/or replacements in a predetermined endogenous targeted DNA sequence, and/or to make single or multiple nucleotide substitutions in a predetermined endogenous target DNA sequence so that the resultant recombined sequence (i.e., a targeted recombinant endogenous sequence) incorporates some or all of the sequence information of the nonhomologous portion of the targeting polynucleotide(s). Additions and deletions may be as small as 1 nucleotide or may range up to about 2 to 10 kilobases or more.

In one application, a targeting polynucleotide can be used to repair a mutated sequence of a structural gene by replacing it or converting it to a wild-type sequence (e.g., a sequence encoding a protein with a wild-type biological activity). For example, such applications could be used to convert a sickle cell trait allele of a hemoglobin gene to an allele which encodes a hemoglobin molecule that is not susceptible to sickling, by altering the nucleotide sequence encoding the β-subunit of hemoglobin so that the codon at position 6 of the β subunit is converted Valβ6→Gluβ6 (Shesely et al. (1991) op.cit.). Other genetic diseases can be corrected, either partially or totally, by replacing, inserting, and/or deleting sequence information in a disease allele using appropriately selected exogenous targeting polynucleotides.

Gene Inactivation

In addition to correcting disease alleles, exogenous targeting polynucleotides can be used to inactivate one or more genes in a cell (or transgenic nonhuman animal).

Once the specific target genes to be modified are selected, their sequences will be scanned for possible disruption sites (convenient restriction sites, for example). Plasmids are engineered to contain an appropriately sized gene sequence with a deletion or insertion in the gene of interest and at least one flanking homology clamp which substantially corresponds or is substantially complementary to an endogenous target DNA sequence. Vectors containing a targeting polynucleotide sequences are typically grown in *E. coli* and then isolated using standard molecular biology methods, or may be synthesized as oligonucleotides. Direct targeted inactivation which does not require vectors may also be done. When using microinjection procedures it is preferable to use a transfection technique with linearized sequences containing only modified target gene sequence and without vector or selectable sequences. The modified gene site is such that a homologous recombinant between the exogenous targeting polynucleotide and the endogenous DNA target sequence can be identified by using carefully chosen primers and PCR, followed by analysis to detect if PCR products specific to the desired targeted event are present (Erlich et al., (1991) *Science* 252: 1643, which is incorporated herein by reference). Several studies have already used PCR to successfully identify and then clone the desired transfected cell lines (Zimmer and Gruss, (1989) *Nature* 338:150; Mouellic et al., (1990) *Proc. Natl. Acad. Sci. USA* 87:4712; Shesely et al., (1991) *Proc. Natl. Acad. Sci. USA* 88:4294, which are incorporated herein by reference). This approach is very effective when the number of cells receiving exogenous targeting polynucleotide(s) is high (i.e., with microinjection, or with liposomes) and the treated cell populations are allowed to expand to cell groups of approximately $1\times10^4$ cells (Capecchi, (1989) *Science* 244:1288). When the target gene is not on a sex chromosome, or the cells are derived from a female, both alleles of a gene can be targeted by sequential inactivation (Mortensen et al., (1991) *Proc. Natl. Acad. Sci. USA* 88:7036).

Homologous Pairing of Targeting Polynucleotides Having Chemical Substituents Exogenous targeting polynucleotides that have chemical substituents may be introduced along with recombinase (e.g., recA) into a metabolically active eukaryotic cell to homologously pair with a predetermined endogenous DNA target sequence in the cell. Typically such exogenous targeting polynucleotides are biotinylated or digoxigenylated, and additional chemical substituents are attached to streptavidin or antidigoxigenin antibodies, respectively, and are thus localized to a specific endogenous target sequence where they produce an alteration or chemical modification to a local DNA sequence. Preferred attached chemical substituents to streptavidin or antidigoxigenin antibodies include: cross-linking agents, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, base-modification agents, immunoglobulin chains, and oligonucleotides. Iron/EDTA chelates are particularly preferred chemical substituents where local cleavage of a DNA sequence is desired (Hertzberg et al. (1982) *J. Am. Chem. Soc.* 104: 313; Hertzberg and Dervan (1984) *Biochemistry* 23: 3934; Taylor et al. (1984) *Tetrahedron* 40: 457; Dervan, P. B. (1986) *Science* 232: 464, which are incorporated herein by reference).

In addition to biotin-streptavidin and digoxigenin-antidigoxigenin AB, other linkage chemistries may be used at the discretion of the practitioner (Corey and Schultz (1988) *Science* 238: 1401, which is incorporated herein by reference).

The broad scope of this invention is best understood with reference to the following examples, which are not intended to limit the invention in any manner.

EXPERIMENTAL EXAMPLES

Homologous Targeting of recA-Coated Polynucleotides in Cells

Homologously targeted exogenous targeting polynucleotides specifically target human DNA sequences in intact nuclei of metabolically active cells. RecA-coated complementary exogenous targeting polynucleotides were introduced into metabolically active human cells encapsulated in agarose microbeads and permeabilized to permit entry of DNA/protein complexes using the Jackson-Cook method (Cook, P. R. (1984) *EMBO J.* 3: 1837; Jackson and Cook (1985) *EMBO J.* 4: 919; Jackson and Cook (1985) *EMBO J.* 4: 913; Jackson and Cook (1986) *J. Mol. Biol.* 192: 65; Jackson et al. (1988) *J. Cell. Sci.* 90: 365, which are incorporated herein by reference). These experiments were designed to specifically target homologous DNA sequences with recA protein in intact nuclei of metabolically active human HEp-2 cells.

Jackson and Cook previously demonstrated that the nuclear membranes of human or other cells may be permeabilized without loss of metabolic function if the cells are first encapsulated in a gel of agarose microbeads. The agarose microbead coat contains the cell constituents and preserves native conformation of chromososomal DNA, while permitting diffusion of macromolecules into and out of the cell compartment. Wittig et al.(1991) *Proc. Natl. Acad. Sci. (U.S.A.)* 88: 2259, which is incorporated herein by reference, demonstrated that monoclonal antibodies directed against left-handed Z-DNA could be diffused into these agarose-embedded cells, and that the antibodies were specifically targeted to chromosomal sequences and conformations. In a similar manner, we incubated biotin- or FITC-labeled complementary DNA targeting polynucleotides coated with recA with agarose-coated cell nuclei and verified the correct homologous targeting of the exogenous targeting polynucleotides to specific predetermined human DNA sequences in cell nuclei of metabolically active cells.

RecA-mediated homologous gene targeting with complementary oligonucleotides in intact human cell nuclei was verified directly by homologous targeting using targeting polynucleotides that were biotinylated. These were subsequently labeled with a fluorescent compound to verify homologous pairing at specific locations having the predetermined sequence(s). RecA-coated targeting polynucleotides for human chromosome 1 pericentrometric alpha-satellite DNA sequences were specifically targeted to chromosome 1 centromere sequences in living human cell nuclei that were permeabilized and suspended in agarose.

In these experiments, recA-coated biotinylated exogenous targeting polynucleotides containing homologous sequences to human chromosome 1 alpha satellite DNA were incubated with human HEp-2 cells. The cells were embedded in agarose, then treated with standard buffers (according to Jackson and Cook, op.cit.) to remove the cytoplasmic membrane and cytoplasm immediately before the addition of targeting polynucleotide coated with recA protein.

The experiments were performed with the following results.

First, in order to test protocols to be used in nuclear encapsulation, freshly trypsinized growing human HEp-2 tumor cells were suspended in complete DMEM encapsulated in a mixture of agarose (2.5%, Fisher-Bioteck) and complete DMEM media adapting the protocols of Nilsson et al., 1983, so that the final agarose concentration was 0.5% (4 volumes cells in suspension with 1 volume 2.5% agarose), and the final cell concentration range was approximately $2.4 \times 10^7$ to $8 \times 10^5$. The encapsulated cells in agarose "beads" were placed in petri dishes to which DMEM complete media was added and were allowed to grow for 24 hr in an incubator at 37° C., 7% $CO_2$. At 24 hr, the cells were clearly growing and multiplying and thus were alive and metabolically active.

An aliquot of agarose containing cells (in beads in DMEM medium) was treated to remove the cytoplasmic membrane and cytoplasm by addition of ice-cold sterile PBS, New Buffer (Jackson et al. (1988) op.cit.: 130 mM KCl, 10 mM $Na_2HPO_4$, 1 mM $MgCl_2$, 1 mM $Na_2ATP$, and 1 mM dithithreitol, pH 7.4 ), New Buffer with 0.5% Triton-X 100, New Buffer with 0.2% BSA, then was centrifuged at low speed using protocols developed by Jackson and Cook, 1985 and 1986 op.cit.; Wittig et al. (1989) *J. Cell. Biol.* 108: 755; Wittig et al. (1991) op.cit.) who have shown that this treatment allows the nuclear membrane to remain morphologically intact. The nuclei are metabolically active as shown by a DNA synthesis rate of 85 to 90% compared with that of untreated control cells.

Cytoplasm was effectively removed by the above treatment, and the encapsulated nuclei were intact as demonstrated by their morphology and exclusion of 0.4% trypan blue. Nuclei in agarose were returned to the humidified $CO_2$ incubator at 37° C. for 24 hr and remained metabolically active. We observed that filtered, sterile mineral oil used in the emulsification process was difficult to remove entirely and interfered with the microscopic visualization of suspended nuclei. Therefore, the cell-agarose suspension process was simplified. In subsequent experiments cells were gently vortexed with melted (39° C.) agarose, then the agarose-cell mixture was sterilely minced before New Buffer treatments. This simpler process, eliminating the oil step, makes it easier to visualize the cells and chromosomes at the completion of reactions.

After mincing of the agar and New Buffer treatments of the cells, the above protocols were used to homologously target endogenous DNA sequences in encapsulated nuclei as follows: 16.5 µl recA-coated (or non-recA-coated control) nick-translated DNA (labeled with biotin-14-dATP) targeting polynucleotide was prepared and bound under standard native recA protocols (see U.S. patent application Ser. No. 07/755,462). Minced agarose fragments were centrifuged and New Buffer supernatant removed. The fragments were resuspended in 1 X AC buffer in a 1.5-ml Eppendorf tube, then centrifuged for removal of the buffer (leaving an estimated 50 to 75 µl of buffer), and prepared targeting poiynucleotide was mixed with the fragments of agarose-containing nuclei. Reactions were incubated in a 37° C. water bath for 2 to 4 hr, then washed, incubated in standard preblock solution, then in preblock supplement with 10 µg/ml FITC-avidin (Vector, DCS grade), and again washed. Experimental results were analyzed by placing a minute amount of a reaction with 3 to 4 µl antifade on a slide with slide cover and viewing it by using the Zeiss CLSM-10 confocal laser scanning microscope (CLSM). Completed reactions were also stored in a refrigerated for later examination.

In the first in vivo experiment, metabolically active HEp-2 cells suspended in 1×PBS were encapsulated in agarose by gentle vortexing, treated using New Buffer protocols, then incubated for 3 hr 15 min with 100 ng of recA-coated targeting polynucleotide specific for Chromosome 1 alpha-satellite DNA biotinylated with bio-14-dATP by nick translation (BRL, Nick Translation Kit) using pUC 1.77 plasmid DNA. We observed specific targeting by the alpha-satellite targeting polynucleotide to pericentromeric chromosome 1 targets in intact nuclei of metabolically active cells. The signals were essentially identical to those using the same targeting polynucleotide with Carnoy's fixed HEp-2 cell targets in suspension. FIGS. 1 and 2 show specific signals in several metabolically active cells from this experiment.

In the second in vivo experiment, cells suspended in incomplete DMEM media instead of 1×PBS were encapsulated in agarose and treated with 62.5 ng of the same targeting polynucleotide used in the first experiment described above and 62.5 ng of a freshly biotinylated targeting polynucleotide prepared under the same protocols. In this experiment, the minced agarose fragments were not resuspended in 1×AC buffer before addition of targeting polynucleotide and some nuclei disintegrated, especially with subsequent centrifugation. The results show that in the nuclei that remained intact, the targeting polynucleotides coated with recA specifically targeted predetermined human DNA targets. In contrast, targeting polynucleotides in reactions without recA did not correctly target the predetermined human DNA sequences. When the targeted DNA (generated from the recA-coated targeting polynucleotides) was decondensed from the nuclei, the alpha-satellite repeat sequences showed precise and evenly spaced signals along the "string" of the alphoid satellite DNA sequences.

Thus, the recA-coated targeting polynucleotides were targeted to the repetitive alpha satellite sequences of Chromosome 1. This result showed DNA targeting in intact nuclei to specific human Chromosome 1 sequences. An example of the experimentally extended DNA with specific alpha-satellite signals appears in FIG. 3.

In the third experiment, cells were suspended in 1×PBS or in incomplete DMEM media before vortexing with agarose and were tested using 62.5 ng of targeting polynucleotide in reactions with and without recA protein. In addition, the reactions were divided in half and washed and FITC-avidin treated in either buffer adjusted to pH 7 or pH 7.4. Cells were incubated with the recA coated targeting polynucleotide for 3 hr 25 min. Live nuclei treated with targeting polynucleotide alone without recA showed no signals. In the recA-treated reactions, relatively weak signals were observed in nuclei incubated in 1×PBS, whereas very strong specific signals were present in nuclei that had been incubated in incomplete DMEM. There was clearly far more signal present in nuclei that were washed and treated with FITC-avidin at pH 7.4 compared with nuclei incubated at pH 7.0. FIG. 4 shows nuclei that were treated with recA coated targeting polynucleotides and incubated at both pH 7.4 and 7.0.

In a fourth experiment, HEp-2 cells were embedded in agarose prepared with 1×PBS, New Buffer treated, then treated with 100 ng of biotinylated targeting polynucleotide complementary to Chromosome 1 alpha-satellite DNA. Controls in this experiment also included reactions without recA protein and additional control reactions supplemented with an identical amount of BSA protein to replace the recA protein. Additionally, cells were also embedded in agarose prepared with 1×AC buffer. Examples of specific targeting to endogenous target sequences were recorded.

In a fourth experiment, we directly determined if the embedded nuclei under the conditions used above were metabolically active. The nuclei in agarose were incubated with bio-21-rUTP in complete medium, then incubated for 2 days in the humidified $CO_2$ atmosphere. After 2 days at 37° C., the cells were examined. Bio-21-rUTP was incorporated in RNA and incubated with FITC-streptavidin. FITC was specifically associated with nucleoli indicative of ribosomal RNA biosynthesis, thus directly showing metabolic activity in these human cells. Similar results were obtained using DNA precursors to measure DNA synthesis. In this experiment it was clear that the majority of nuclei in the PBS agarose reaction had condensed chromosomes. There was nuclear division in a number of these nuclei also, indicative of full metabolic viability, which was also shown in the AC buffer-treated cells.

A fifth experiment was performed using, again, HEp-2 cells embedded in agarose. Final concentration of the cells in agarose was 3.7×10$^6$/ml. The cells were suspended in 1×PBS prior to combining with agarose. The final agarose concentration was 0.5%. There were two reactions, one in which recA was used to coat targeting polynucleotide, the second in which recA protein was replaced by New Buffer at the same protein concentration followed by New Buffer treatments to remove the cytoplasm. The nuclei in agarose were incubated for 3 hr with targeting polynucleotide, then processed for detection of correctly targeted polynucleotide using the protocols describe previously. FITC-avidin was used to visualize the biotinylated targeting polynucleotide at a concentration of 20 ng/ml. Results showed that cells with the recA-coated complementary targeting polynucleotide displayed specific signals in 25% or more of the intact nuclei. In contrast, the BSA-treated controls did not show any signal.

Cells in agarose from this experiment were further incubated at 37° C. in the $CO_2$ incubator in complete medium. At 22 hr, these cells were metabolically active. Chromosomes were condensed, and a number of nuclei were in the process of dividing. In these experiments, a significant number of the cells incubated with recA-coated complementary targeting polynucleotides showed specific signal, whereas 0% of the cells incubated with targeting polynucleotide alone showed specific signal.

In summary, recA-coated biotinylated targeting polynucleotides for human chromosome 1 alpha-satellite DNA were specifically targeted to human HEp-2 epithelial carcinoma chromosomal DNA in intact cell nuclei of metabolically active cells that had been suspended in agarose, then treated with buffers and recA-coated targeting polynucleotides under suitable reaction conditions (supra and U.S. patent application Ser. No. 07/755,462 and U.S. patent application Ser. No. 07/520,321, incorporated herein by reference). Specific binding by the recA-coated targeting polynucleotide to chromatin alpha-satellite DNA was observed only in the agarose embedded nuclei which were incubated with recA-coated targeting polynucleotides. Control nuclei incubated with targeting polynucleotides in the absence of recA and/or with nonspecific protein exhibited no signal.

Targeting of Human p53 Gene

We performed recA-mediated homologous targeting of biotinylated targeting polynucleotides that were homologous to the human p53 tumor supressor gene, and compared the results to targeting of alpha satellite DNA sequences in human chromosome 1. In these experiments, exponentially growing cells were trypsinized, washed, suspended in incomplete medium and encapsulated in agarose. The agarose was minced into pieces with a razor blade and the encapsulated cells were treated with New Buffer. A sample from each group was removed to verify that nuclei were intact.

Nuclei were washed in 1×AC buffer and incubated with recA-coated complementary single-stranded DNA oligonucleotides (i.e., exogenous targeting polynucleotides) for 3.5 hours at 37° C. The alpha satellite DNA targeting poynucleotides for chromosome 1 were previously described and were nick-translated with biotinylated deoxyribonucleotides (bio-14-dATP). The p53 tumor suppressor gene polynucleotide was obtained from Oncor (209 Perry Parkway, Gaithersburg, Md. 20877) and is a 1.2 kilobase cDNA fragment from a wild-type human p53 gene (Fields and Jang, (1990) *Science* 242: 1046; Miller et al. (1986) *Nature* 319: 783; Zakut-Houre et al. (1985) *EMBO J.* 4: 1251). The 1.2 kilobase human p53 DNA was nick-translated with biotinylated deoxyribonucleotides and yielded a population of biotinylated targeting polynucleotides having a size range (about 100 to 600 nucleotides) similar to that obtained for the human chromosome 1 alpha satellite targeting polynucleotides. The targeting polynucleotides were separately incubated with encapsulated cells. Following incubation 3 washes of 1.75×SSC were done, and sampled nuclei were verified as intact after the washing step. After washing, the targeted encapsulated cell nuclei were incubated in preblock and FITC-avidin was added to preblock buffer to a final concentration of 20 μg/ml for 15 minutes. The targeted encapsulated cell nuclei were washed sequentially in 4×SSC, 4×SSc with 0.1% Triton X-100., and then 4×SSC. Samples of nuclei were again taken and used to verify that the targeted nuclei were metabolically active. Microscopic examination showed that metabolically active cells contained specific FITC-targeting polynucleotide:targeted endogenous sequence complexes (shown in FIG. 5). The p53 targeting polynucleotides were specifically targeted to human chromosome 17, the location of the endogenous human p53 gene sequences, indicating specific pairing of a targeting polynucleotide to a unique endogenous DNA target sequence. The human chromosome 1 alpha satellite DNA was also specifically targeted to the chromosome 1 pericentromeric satellite sequences.

The experiments validated a highly specific DNA targeting technique for human or other cells as evidenced by homologous sequence targeting techniques in metabolically active cells. The targeting technique employs the unique properties of recA-mediated DNA sequence targeting with single-stranded (complementary) short targeting polynucleotides. Native intact nuclei were incubated with labeled, heat-denatured targeting polynucleotides coated with recA protein. The DNA hybridized to the predetermined targeted homologous sequences. In these experiments, the targeting polynucleotides formed heteroduplexes with specific gene sequences within metabolically active cell nuclei. This in vivo targeting by recA-mediated homologous targeting polynucleotides shows the targeting specificity and therapeutic potential for this new in vivo methodology. Application of recA or other recombinase-mediated targeting of (complementary) ssDNA or denatured dsDNA targeting polynucleotides to predetermined endogenous DNA targets is important for human gene entry, gene knockout, gene replacement, and gene mutation or correction.

Correcting a Mutant Gene to Produce a Functional Gene Product

Homologously targeted complementary DNA oligonucleotides were used to correct 10 bp insertion mutations in vector genes and restore vector gene expression and vector protein function in microinjected mammalian cells.

Experiments were designed to test whether homologously targeted complementary 271-bp oligonucleotide targeting polynucleotides could correct a 10-bp insertion mutation in the lacZ gene of a mammalian DNA vector which encoded a nonfunctional β-galactosidase, so that a corrected lacZ gene encoded and expressed a functional enzyme. Functional enzyme (β-galactosidase) was detected by an X-gal assay that turns cells expressing a revertant (i.e., corrected) lacZ gene a blue color.

NIH3T3 cells microinjected with the mutant test vector bearing a 10 basepair insertion in the lacZ coding sequence do not produce any detectable functional β-galactosidase enzyme. In contrast, cells microinjected with the wild type test vector do produce functional enzyme.

We obtained the functional lac plasmid pMC1lacpa for use as a positive control for expression of β-galactosidase. pMC1lacXpa is the target test mutant plasmid (shown in FIG. 6). It is identical to pMC1lacpa (shown in FIG. 7) but has a 10-bp XbaI linker insertional mutation. This plasmid does not express β-galactosidase activity in mouse NIH3T3 cells when introduced by electroporation. It does not produce blue color in the presence of X-GAL indicative of β-galactosidase production following vector microinjection. Negative controls with mock or noninjected cells we also done. Using these controls and NIH3T3 cells have no detectable background blue staining.

The plasmid pMC1lacpa (8.4 kb) contains the strong polyoma virus promoter of transcription plus ATG placed in front of the lacZ gene. The polyadenylation signal from SV40 virus was placed in back of the lacZ gene. The plasmid vector was pIB130 (shown in FIG. 8) from IBI (New Haven, Conn.). The mutant vector pMC1lacpa has a 10-bp insertion in the XbaI site. This mutation consists of the inserted sequence CTCTAGACGCG (see FIG. 9).

In several control microinjection experiments using pMC1lacXpa we consistently failed to detect any blue microinjected cells. in contrast, in various experiments approximately 8 to 13% of the 3T3 cells injected with pMC1lacpa DNA expressed β-galactosidase as evidenced by their blue color. No cells microinjected with injection buffer alone or mock injected were observed as blue.

We synthesized 20-bp primers for producing a 271-bp PCR product (see FIG. 9) from the wild-type lacZ sequence for use as targeting polynucleotides. We chose this 271-bp fragment to span the 10 bp insertion mutation as a nonhomologous sequence. The 271-bp DNA oligonucleotide was separated by gel electrophoresis and electroeluted from agarose, ethanol precipitated, and its concentration determined by absorbance at 260 nm. The 271-bp fragment was 5' end-labeled with $^{32}p$ and specifically D-looped with the pMC1lacXpa or pMC1lacpa plasmid DNA using recA as shown by agarose gel electrophoresis.

Experiments were designed to test for β-galactoside production in cells microinjected with pMC1lacXpa vectors with targeting polynucleotide-target complexes using complementary 271-bp oligonucleotide targeting polynucleotide treated with recA. The 271-mer targeting polynucleotides in 1×TE buffer were denatured by heating at 100° C. for 5 min and immediately quenched in an ice bath for 1 min. The DNA solution was collected at 4° C. by centrifugation. RecA-mediated targeting polynucleotide reactions containing a final volume of 10 μl were assembled using 1.0 μl 10×AC buffer, 1.5 μl 16 mM ATPγS, 3.8 μl dd $H_2O$, 1.2 μl recA protein solution (13 μg/μl), and 2.5 μl of 271 bp denatured targeting polynucleotide. The recA protein was allowed to coat the DNA for 10 min at 37° C. Next, 1.0 μl of 10×AC buffer, 1.0 μl of 0.2M magnesium acetate, 1.3 μl of pMC1lacXpa (1.0 μg/μl), and 6.7 μl of dd $H_2O$ was added to a final volume of 20 μl. Control reactions were performed without added recA protein.

NIH3T3 cells were capillary needle microinjected with targeting polynucleotide-target DNA mixtures loaded in glass pipettes freshly pulled into microneedles using a Sutter instruments microprocessor controlled apparatus. An ECET Eppendorf microinjection pump and computerized micromanipulator were used for computer-assisted microinjection using an Olympus IMT-2 inverted microscope. Cells were carefully microinjected under controlled pressure and time. NIH3T3 cells injected with pMC1lacpa showed approximately 9% of the injected cells were blue. None (0%) of the cells injected with pMC1lacXpa DNA in reactions containing the 271 bp oligonucleotide but without recA protein showed a blue color. In marked contrast, approximately 1% of the cells microinjected with the recA-mediated 271-bp targeting polynucleotide targeted to the pMC1lacXpa target hybrid were blue. Thus., these measurements indicate that the mutant pMC1lacXpa gene can be targeted and corrected by the 271-bp oligonucleotide, which has been targeted with recA-coated targeting polynucleotides. In summary, these measurements show that the 10 bp Xba I insertion mutation can be corrected with the recA-mediated targeted corrected in vivo, but not with the 271-bp oligonucleotide alone. Note that the in situ identification of 3T3 cells expressing β-galactosidase was performed following incubation with X-gal (5-bromo-4-chloro-3-indolyl-β- galactopyranoside) (Sigma), as described by Fischer et al. (1988) *Nature* 332: 853; Price et al. (1987) *Proc. Natl. Acad. SCi. (U.S.A.)* 84: 156; Lim and Chae (1989) *Biotechniques* 7: 576.

Although the present invention has been described in some detail by way of illustration for purposes of clarity of understanding, it will be apparent that certain changes and modifications may be practiced within the scope of the claims.

We claim:

1. A method for targeting and altering, by homologous recombination, a pre-selected target DNA sequence in a eukaryotic cell to make a targeted sequence modification, said method comprising the steps of:

introducing into at least one eukaryotic cell at least one recA recombinase and at least two single-stranded targeting polynucleotides which are substantially complementary to each other, and which further comprise a homology clamp that substantially corresponds to or is substantially complementary to a preselected target DNA sequence; and identifying a eukaryotic cell having a targeted DNA sequence modification at a preselected target DNA sequence.

2. A method according to claim 1, wherein at least two targeting polynucleotides which are substantially complementary to each other and comprise double-stranded DNA are used.

3. A method according to claim 2, wherein a first said targeting polynucleotide comprises a homology clamp that is complementary to said preselected target DNA sequence and a second said targeting polynucleotide comprises a homology clamp that corresponds to said preselected target DNA sequence.

4. A method according to claim 3, wherein said first targeting polynucleotide consists of a homology clamp.

5. A method according to claim 3, wherein the homology clamp of said first targeting polynucleotide and the homology clamp of said second targeting polynucleotide are complementary.

6. A method according to claim 2, wherein a first said targeting polynucleotide comprises a homology clamp that is complementary to a preselected target DNA sequence.

7. A method according to claim 6, wherein a second targeting polynucleotide comprises a homology clamp that is complementary to a sequence of said first targeting polynucleotide.

8. A method according to claim 7, wherein said second targeting polynucleotide consists of a sequence that is complementary to the complete sequence of said first polynucleotide.

9. A method according to claim 1, wherein said step of introducing is carried out by electroporation, lipofection, microinjection, biolistics, or calcium phosphate-mediated transfection.

10. A method according to claim 9, wherein said recA recombinase is a wildtype E. coli recA or recA803.

11. A method according to claim 1, wherein said recA recombinase is E. coli recA.

12. A method according to claim 1, wherein said recA recombinase is noncovalently bound to said targeting polynucleotide.

13. A method according to claim 1, wherein said targeting polynucleotide comprises a homology clamp that is complementary to said preselected target DNA sequence.

14. A method according to claim 13, wherein the targeting polynucleotide consists of a homology clamp.

15. A method according to claim 1, wherein the preselected target DNA sequence is a transcribed sequence.

16. A method according to claim 1, wherein the preselected target DNA sequence is unique in a haploid genome of said eukaryotic cell.

17. A method according to claim 16, wherein the preselected target DNA sequence is unique in a diploid genome of said eukaryotic cell.

18. A method according to claim 1, wherein the targeted sequence modification comprise s a deletion of at least one nucleotide.

19. A method according to claim 18, wherein the targeted sequence modification comprises a deletion of about ten consecutive nucleotides.

20. A method according to claim 1, wherein the recA recombinase and the targeting polynucleotide are introduced into the eukaryotic cell simultaneously.

21. A method according to claim 20, wherein the recA recombinase and the targeting polynucleotide are introduced into the eukaryotic cell by microinjection.

22. A method according to claim 21, wherein the recA recombinase and the targeting polynucleotide are preincubated prior to introduction into the eukaryotic cell.

23. A method according to claim 1, wherein the targeted sequence modification creates a sequence that encodes a polypeptide having a biological activity.

24. A method according to claim 23, wherein the biological activity is an enzymatic activity.

25. A method according to claim 1, wherein the targeting polynucleotide is produced by oligonucleotide synthesis or nick-translation of a template polynucleotide.

26. A method according to claim 1, wherein the targeting polynucleotide comprises a homology clamp that is at least about 50 nucleotides long.

27. A method according to claim 1, wherein said step of identifying said targeted cell is accomplished by detection of the targeted DNA sequence modification by phenotype selection comprising selection for cells expressing a neo or HSV-tk drug-resistance gene.

28. A method for targeting an exogenous polynucleotide having a chemical substituent to a substantially homologous target DNA sequence in a nucleus of a metabolically active eukaryotic cell, comprising the steps of:

introducing into a nucleus of a metabolically active cell at least one recA recombinase and at least one exogenous polynucleotide having a chemical substituent and a sequence that substantially corresponds to or is substantially complementary to a preselected target DNA sequence; and incubating the metabolically active cell under suitable reaction conditions whereby the exogenous polynucleotide is targeted to the endogenous target sequence.

29. A method according to claim 28, wherein said recA recombinase is *E. coli* recA.

30. A method according to claim 28, wherein said recA recombinase is noncovalently bound to said targeting polynucleotide.

31. A method according to claim 28, wherein the exogenous polynucleotide polynucleotide comprises a chemical substituent which is not genotoxic.

32. A method according to claim 31, wherein the chemical substituent is not cytotoxic.

33. A method according to claim 32, wherein the chemical substituent does not cleave DNA.

34. A method according to claim 28, wherein the chemical substituent comprises a biotinylated nucleotide.

35. A method according to claim 28, wherein the exogenous polynucleotide hybridizes to a sequence that is repeated in the genome of the metabolically active cell.

36. A method according to claim 35, wherein the sequence is present in satellite DNA repetitive sequences.

37. A method according to claim 28, wherein at least two exogenous polynucleotides which are substantially complementary to each other are used.

38. A method according to claim 28, wherein each exogenous polynucleotide comprises a chemical substituent.

39. A method according to claim 28, wherein the exogenous polynucleotide is generated by nick-translation of a polynucleotide template.

40. A method according to claim 28, wherein the step of incubating is performed in an embedding medium.

41. A method according to claim 28, wherein the metabolically active cells are permeabilized.

42. A method according to claim 28, wherein the cells are embedded in agarose microbeads.

43. A method according to claim 28, wherein the target DNA sequence is a human oncogene or tumor suppressor gene sequence.

44. A method according to claim 43, wherein the target DNA sequence is a human p53 sequence.

45. A method for targeting and altering, by homologous recombination, a pre-selected target DNA sequence in a eukaryotic cell to make a targeted sequence modification, said method comprising the steps of:

introducing into at least one eukaryotic cell at least one recA recombinase and at least one double-stranded targeting polynucleotide having a homology clamp that substantially corresponds to or is substantially complementary to a preselected target DNA sequence; and identifying a eukaryotic cell having a targeted DNA sequence modification at a preselected target DNA sequence.

46. A method for targeting and altering, by homologous recombination, a pre-selected target nucleic acid sequence in a eukaryotic cell to make a targeted sequence modification, said method comprising the steps of:

administering or directly introducing into at least one eukaryotic cell at least one recA recombinase and at least two single-stranded targeting polynucleotides which are substantially complementary to each other, and which further comprise a homology clamp that substantially corresponds to or is substantially complementary to a preselected target nucleic acid sequence; and identifying a eukaryotic cell having a targeted nucleic acid sequence modification at a preselected target DNA sequence.

47. A method for targeting and altering, by homologous recombination, a pre-selected target nucleic acid sequence in a eukaryotic cell to make a targeted sequence modification, said method comprising the steps of:

administering or introducing into at least one eukaryotic cell at least two single-stranded targeting polynucleotides which are substantially complementary to each other, and which further comprise a homology clamp that substantially corresponds to or is substantially complementary to a preselected target nucleic acid sequence, wherein said single stranded targeting polynucleotides are coated with recA recombinase; and identifying a eukaryotic cell having a targeted nucleic acid sequence modification at a preselected target nucleic acid sequence.

* * * * *